United States Patent
Horti et al.

(10) Patent No.: US 10,912,850 B2
(45) Date of Patent: Feb. 9, 2021

(54) $^{18}$F-FNDP FOR PET IMAGING OF SOLUBLE EPOXIDE HYDROLASE (SEH)

(71) Applicants: THE JOHNS HOPKINS UNIVERSITY, Baltimore, MD (US); OREGON HEALTH & SCIENCE UNIVERSITY, Portland, OR (US)

(72) Inventors: Andrew Horti, Ellicott City, MD (US); Martin G. Pomper, Baltimore, MD (US); Nabil J. Alkayed, West Linn, OR (US)

(73) Assignees: The Johns Hopkins University, Baltimore, MD (US); Oregon Health & Science University, Portland, OR (US)

( * ) Notice: Subject to any disclaimer, the term of this patent is extended or adjusted under 35 U.S.C. 154(b) by 0 days.

(21) Appl. No.: 16/098,694

(22) PCT Filed: May 4, 2017

(86) PCT No.: PCT/US2017/031065
§ 371 (c)(1),
(2) Date: Nov. 2, 2018

(87) PCT Pub. No.: WO2017/192854
PCT Pub. Date: Nov. 9, 2017

(65) Prior Publication Data
US 2019/0134235 A1 May 9, 2019

Related U.S. Application Data

(60) Provisional application No. 62/331,691, filed on May 4, 2016.

(51) Int. Cl.
*A61K 51/04* (2006.01)
*C07D 213/82* (2006.01)
*C07B 59/00* (2006.01)

(52) U.S. Cl.
CPC ........ *A61K 51/0455* (2013.01); *C07B 59/002* (2013.01); *C07D 213/82* (2013.01); *C07B 2200/05* (2013.01)

(58) Field of Classification Search
CPC .............................. A61K 51/04; C07D 213/82
See application file for complete search history.

(56) References Cited

U.S. PATENT DOCUMENTS

2006/0276515 A1* 12/2006 Cywin ................. C07D 213/82
514/343

FOREIGN PATENT DOCUMENTS

| WO | 20060121719 A2 | 11/2006 | |
|---|---|---|---|
| WO | WO 2006/121719 | 11/2006 | |
| WO | WO-2006121719 A2 * | 11/2006 | ............ C07D 213/56 |

OTHER PUBLICATIONS

Tarik F. Massoud et al., Molecular imaging in living subjects: seeing fundamental biological processes in a new light, Genes and Development, 17, 545-580. (Year: 2003).*
F. Dolle, Fluorine-18-Labelled Fluoropyridines: Advances in Radiopharmaceutical Design, Current Pharmaceutical Design, 11, 3221-3235. (Year: 2005).*
Couto et al., PET Imaging of Epigenetic Influences on Alzheimer's Disease. International journal of Alzheimer's disease. 2015;2015:575078.
Heiss, PET imaging in ischemic cerebrovascular disease: current status and future directions. Neurosci Bull. 2014;30:713-732.
Horti et al., 18F-FNDP for PET Imaging of Soluble Epoxide Hydrolase. J Nucl Med 2016;57:1817-1822.
Iliff et al., Epoxyeicosanoids as mediators of neurogenic vasodilation in cerebral vessels. American journal of physiology Heart and circulatory physiology. 2009;296:H1352-1363.
Iliff et al., Soluble Epoxide Hydrolase Inhibition: Targeting Multiple Mechanisms of Ischemic Brain Injury with a Single Agent. Future neurology. 2009;4:179-199.
Imig et al., An orally active epoxide hydrolase inhibitor lowers blood pressure and provides renal protection in salt-sensitive hypertension. Hypertension. 2005;46:975-981.
Inceoglu et al., Epoxy fatty acids and inhibition of the soluble epoxide hydrolase selectively modulate GABA mediated neurotransmission to delay onset of seizures. PLoS One. 2013;8:e80922.
Innis et al., Consensus nomenclature for in vivo imaging of reversibly binding radioligands. J Cereb Blood Flow Metab. 2007;27:1533-1539.
Knopman et al., Vascular dementia in a population-based autopsy study. Arch Neurol. 2003;60:569-575.
Lee et al., Genetic variation in soluble epoxide hydrolase (EPHX2) and risk of coronary heart disease: The Atherosclerosis Risk in Communities (ARIC) study. Hum Mol Genet. 2006;15:1640-1649.
Logan et al., Graphical analysis of reversible radioligand binding from time-activity measurements applied to [N-11C-methyl]-(-)-cocaine PET studies in human subjects. J Cereb Blood Flow Metab. 1990;10:740-747.
Martini et al., Genetic variation in soluble epoxide hydrolase: association with outcome after aneurysmal subarachnoid hemorrhage. J Neurosurg. 2014;121:1359-1366.
Morris et al., Diagnostic accuracy of F amyloid PET tracers for the diagnosis of Alzheimer's disease: a systematic review and meta-analysis. Eur J Nucl Med Mol Imaging. Feb. 2016;43(2):374-385.
Nelson et al., Role of soluble epoxide hydrolase in age-related vascular cognitive decline. Prostaglandins Other Lipid Mediat. 2014;113-115:30-37.
Newman et al., Epoxide hydrolases: their roles and interactions with lipid metabolism. Prog Lipid Res. 2005;44:1-51.
Rohlfing et al., The INIA19 Template and NeuroMaps Atlas for Primate Brain Image Parcellation and Spatial Normalization. Frontiers in neuroinformatics. 2012;6:27.

(Continued)

*Primary Examiner* — Michael G. Hartley
*Assistant Examiner* — Jagadishwar R Samala
(74) *Attorney, Agent, or Firm* — Casimir Jones, S.C.; Jeffrey W. Childers

(57) ABSTRACT

Radiofluorinated FNDP for PET imaging of soluble epoxide hydrolase (sEH) and method of using the same are disclosed.

22 Claims, 11 Drawing Sheets
(8 of 11 Drawing Sheet(s) Filed in Color)

(56) References Cited

OTHER PUBLICATIONS

Shen et al., Discovery of inhibitors of soluble epoxide hydrolase: a target with multiple potential therapeutic indications. J Med Chem. 2012;55:1789-1808.

Silbert et al., Trajectory of white matter hyperintensity burden preceding mild cognitive impairment. Neurology. 2012;79:741-747.

Sinal et al., Targeted disruption of soluble epoxide hydrolase reveals a role in blood pressure regulation. J Biol Chem. 2000;275:40504-40510.

Spector et al., Action of epoxyeicosatrienoic acids on cellular function. Am J Physiol Cell Physiol. 2007;292:C996-1012.

Sura et al., Distribution and expression of soluble epoxide hydrolase in human brain. J Histochem Cytochem. 2008;56:551-559.

Terashvili et al., Antinociception produced by 14,15-epoxyeicosatrienoic acid is mediated by the activation of beta-endorphin and met-enkephalin in the rat ventrolateral periaqueductal gray. J Pharmacol Exp Ther. 2008;326:614-622.

The National Institute of Mental Health, CNS Radiotracer Table, retrived from https://www.nimh.nih.gov/research/research-funded-by-nimh/therapeutics/cns-radiotracer-table.shtml on Nov. 20, 2019, 8 pages.

ISR and Written Opinion for PCT/US2017/031065, dated Aug. 16, 2017, 15 pages.

International Search Report and Written Opinion dated Aug. 16, 2017, from related PCT Patent Application No. PCT/US2017/031065.

Horti, A.G. et al., "18F-FNDP for PET Imaging of Solluble Epoxide Hydrolase", The Journal of Nuclear Medicine, [Epub] Jul. 14, 2016, vol. 57, No. 11, pp. 1817-1822.

Chemical Abstract, 3-Pyridinecarboxamide, 5-bromo-N-(3,3-diphenylpropyl), Registration No. 852166-15-5, May 13, 2005, 2 pages.

Chemical Abstract, Chemical Abstract, 3-Pyridinecarboxamide, 5-bromo-N-(3,3-diphenylpropyl), No. 1180991-55-2, Sep. 7, 2009, 2 pages.

Eldrup et al., Structure-Based Optimization of Arylamides as Inhibitors of Soluble Epoxide Hydrolase. J Med Chem. Oct. 8, 2009;52(19):5880-95.

Extended European Search Report for EP17793343.9, dated Dec. 6, 2019, 9 pages.

* cited by examiner

18F-FNDP FOR PET IMAGING OF SOLUBLE EPOXIDE HYDROLASE (SEH)

CROSS-REFERENCE TO RELATED APPLICATIONS

This application is a 35 U.S.C. § 371 National Stage Entry of International Application No. PCT/US2017/031065 having an international filing date of May 4, 2017, which claims the benefit of U.S. Provisional Application No. 62/331,691, filed May 4, 2016, the contents of which are incorporated herein by reference in their entirety.

FEDERALLY SPONSORED RESEARCH OR DEVELOPMENT

This invention was made with government support under NS089427 and AG054802 awarded by the National Institutes of Health. The government has certain rights in the invention.

BACKGROUND

Epoxyeicosatrienoic acids (EETs) are signaling molecules important in the vasodilation of cerebral vessels that accompanies neuronal activity. They also modulate the activity of numerous molecular targets and signaling pathways (Spector and Norris, Am. J. Physiol. Cell Physiol 2009). Soluble epoxide hydrolase (sEH), abundantly distributed throughout the mammalian body (Sura et al., J. Histochem. Cytochem, 2008; Marowski et al., Neuroscience, 2009), catalyzes the hydrolysis of EETs to less biologically active molecules (Newman et al., Prog. Lipid. Res., 2005). During the last decade sEH has become a pharmaceutical target and a number of small-molecule sEH inhibitors have been developed. Those sEH inhibitors elevate levels of EETs that in turn could benefit a variety of conditions including hypertension, atherosclerosis, inflammation, diabetes, pain, and pulmonary diseases, among others (Shen and Hammock, J. Med. Chem., 2012).

Regulation of sEH is altered in many conditions, including vascular cognitive impairment (VCI) and stroke, among others. Contribution of cerebrovascular pathology to Alzheimer's disease (AD) and dementia is becoming more appreciated. Post-mortem studies have shown that one third of patients with dementia have co-morbid cerebrovascular pathology (White et al., Ann. NY Acad SCi., 2002; Knopman et al., Arch. Neurol., 2003). A recent report found a 50% greater sEH activity in subjects with VCI versus age-matched controls (Neslon et al., Prostaglandins Other Lipid. Mediat., 2014). The most common type of VCI is associated with white matter hyperintensities that are early predictors of conversion to mild cognitive impairment (Neslon et al., Prostaglandins Other Lipid. Mediat., 2014) that, in turn, represents an increased risk of developing AD.

As noted above, changes in the expression of sEH alter the biological effects of EETs. A consistently observed effect of EETs is their ability to prevent apoptosis following ischemic insult, as well as other forms of injury (Iliff and Alkayed, Future neurology, 2009). Various studies have shown that EETs protect the brain during stroke and that inhibition of sEH enhances this effect (Ingraham et al., Curr. Med. Chem, 2011). Patients suffering aneurysmal subarachnoid hemorrhage are at high risk for delayed cerebral ischemia and stroke (Martini et al., J. Neurosurg., 2014). Patients with the common K55R genetic polymorphism in the sEH gene (Ephx2) demonstrated 30% lower levels of EETs due to increased activity of she (Lee et al., Hum. Mol. Genet., 2006) and they exhibited a mortality of 28.6% after stroke versus 5.3% in the control subjects (Martini et al., J. Neurosurg., 2014). Other studies have demonstrated highly increased expression of sEH in animal models of epilepsy (Hung et al., Brain Behav. Immun., 2015) and Parkinson's disease (Qin et al., Mol. Neurob., 2015).

In addition to facilitating drug development (Shen and Hammock, J. Med. Chem., 2012), the importance of a PET imaging agent targeting sEH resides in gaining a better understanding of stroke and dementia, namely the vascular aspects of the latter, non-invasively, repeatedly and at high resolution. Clinically stroke is evaluated primarily through anatomic and functional magnetic resonance imaging, with molecular approaches limited due to a lack of viable radiotracers for this indication beyond those used to measure perfusion with single photon emission computed tomography (Heiss, Neurosci. Bull., 2014). A PET agent for sEH may enable distinction between AD and VCI in vivo, rather than having to rely on postmortem observation of Aβ plaques and neurofibrillary tangles (Morris et al., Eur. J. Nucl. Med. Mol, Imaging, 2015; Couto and Millis, International Journal of Alzheimer's disease, 2015).

SUMMARY

In some aspects, the presently disclosed subject matter provides a compound of formula (I):

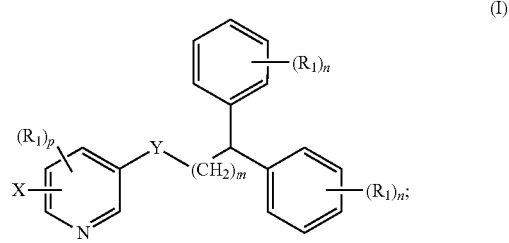

wherein X is selected from the group consisting of F, Br, and I and radioisotopes thereof; Y is —NR—C(=O)— or —C(=O)—NR— m is an integer selected from the group consisting of 1, 2, 3, and 4; n is an integer selected from the group consisting of 1, 2, 3, 4, and 5; p is an integer selected from the group consisting of 1, 2, and 3; R is selected from the group consisting of hydrogen, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; each $R_1$ can independently be the same or different and is selected from the group consisting of hydrogen, halogen, alkoxyl, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted alkylaryl, substituted or unsubstituted naphthyl, and substituted or unsubstituted biphenyl; and stereoisomers or pharmaceutically acceptable salts thereof.

In other aspects, the compound of formula (I) is a compound of formula (II):

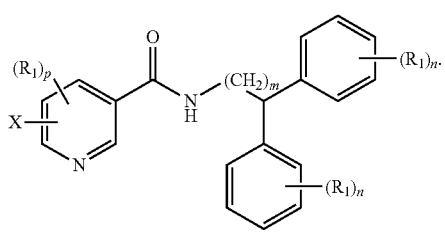

In certain aspects, the compound of formula (I) further comprises a radioactive isotope suitable for imaging.

In particular aspects, the radioactive isotope suitable for imaging is $^{18}$F, $^{76}$Br, $^{123}$I, $^{124}$I, $^{125}$I, and $^{131}$I.

In still more particular aspects, the compound of formula (I) is

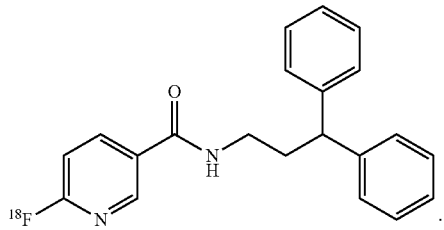 [SMILES: O=C(NCCC(c1ccccc1)c1ccccc1)c1ccc([18F])nc1]

In other aspects, the presently disclosed subject matter provides a method for imaging soluble epoxide hydrolase (sEH), the method comprising contacting sEH with an effective amount of a compound of formula (I), and making an image.

In some other aspects, the presently disclosed subject matter provides a method for inhibiting soluble epoxide hydrolase (sEH) in the treatment of a sEH mediated disease, the method comprising administering to a subject a therapeutically effective amount of a compound of formula (I), thereby inhibiting sEH.

In yet other aspects, the presently disclosed subject matter provides a kit comprising a compound of formula (I).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1A:
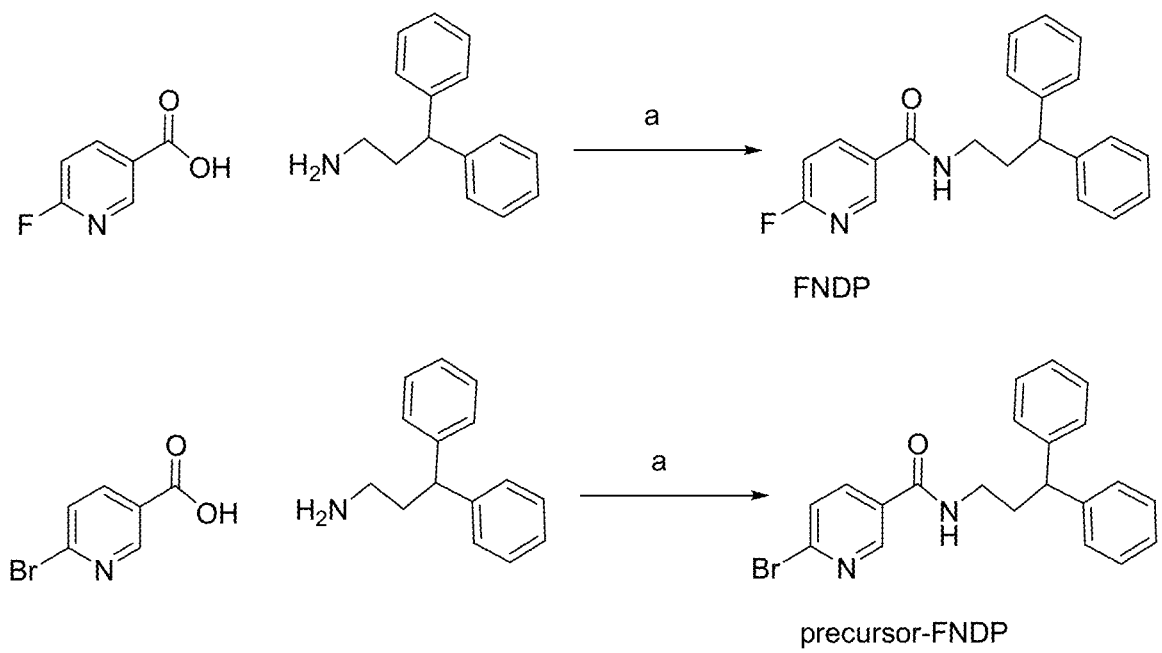
Figure 1B:
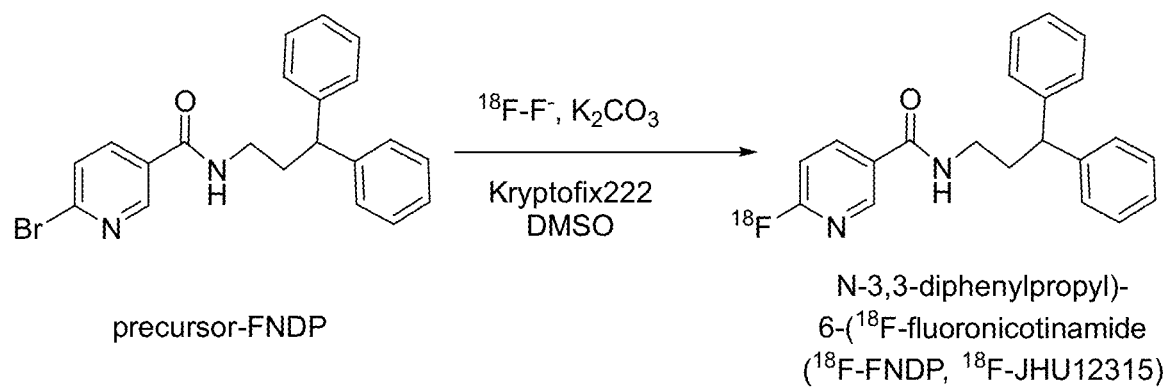
Figure 2:
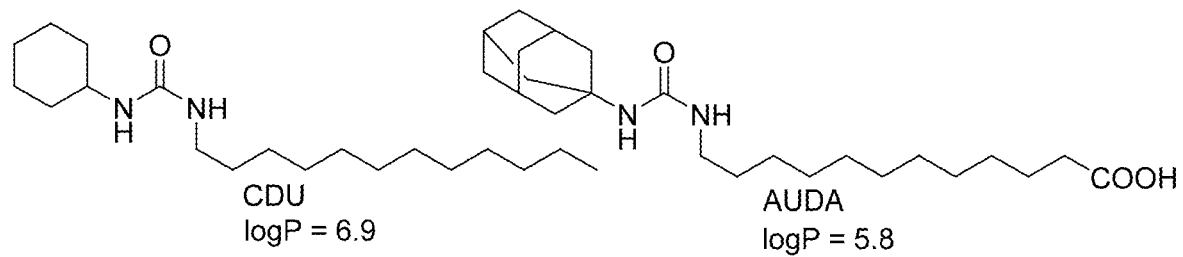
Figure 3:
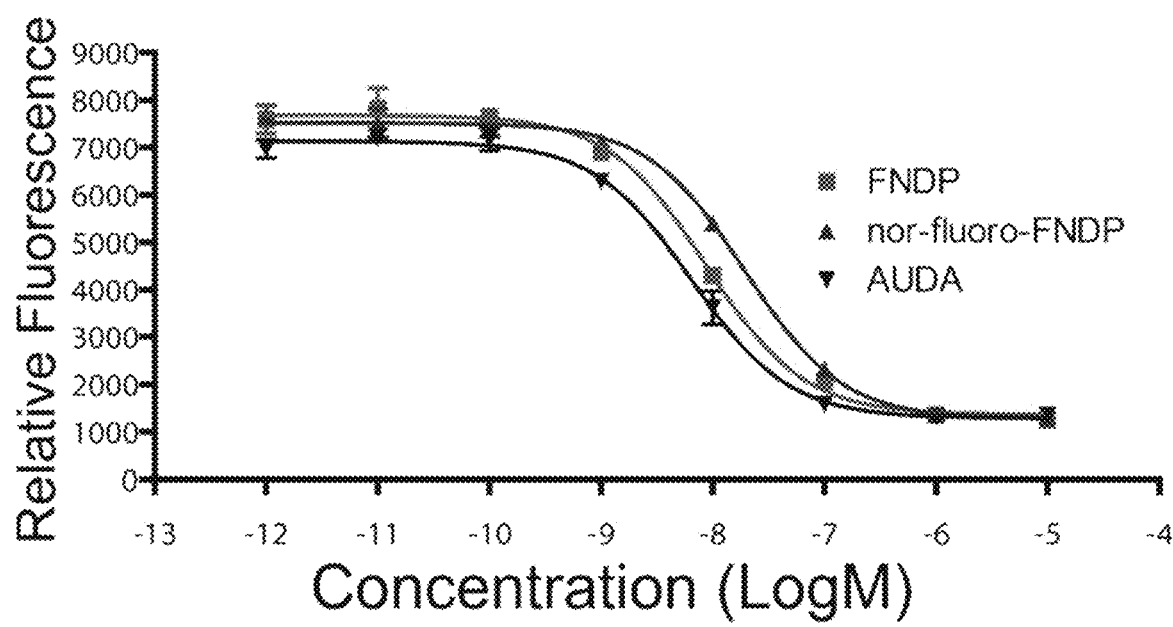
Figure 4:
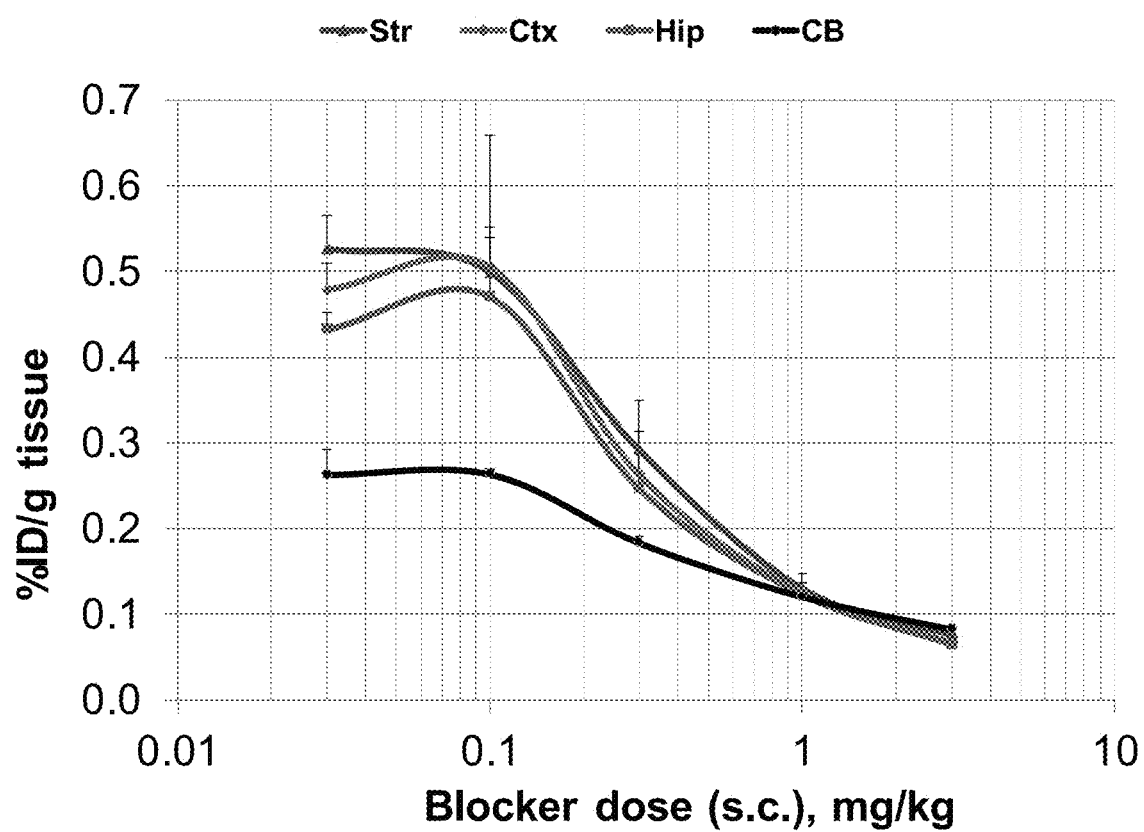
Figure 5:
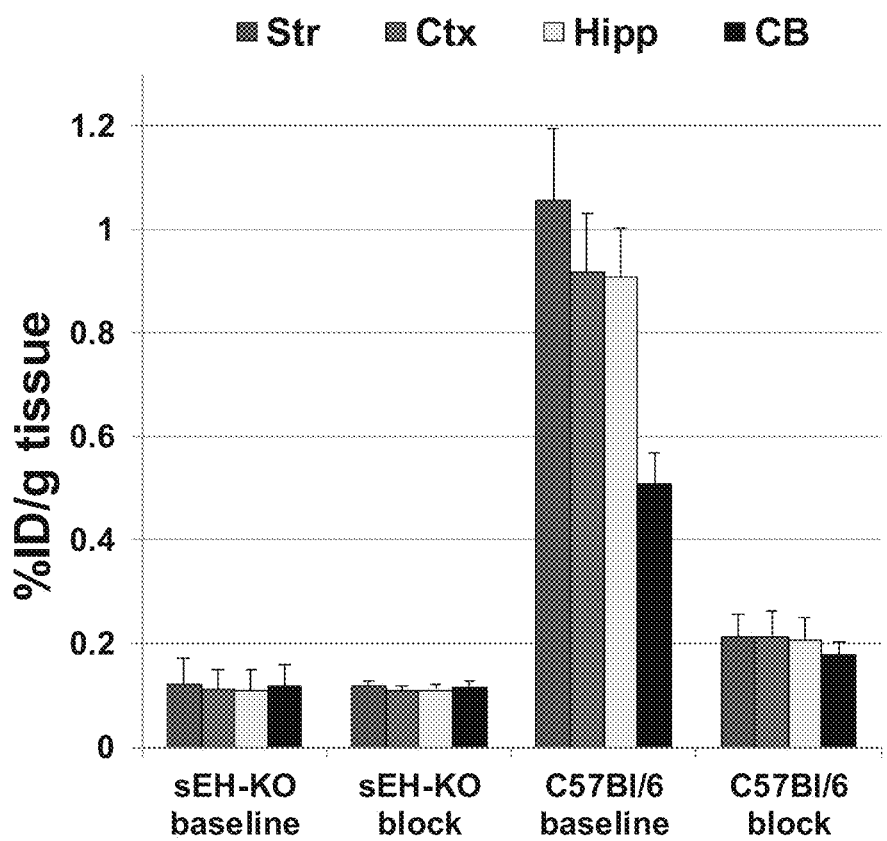
Figure 6:
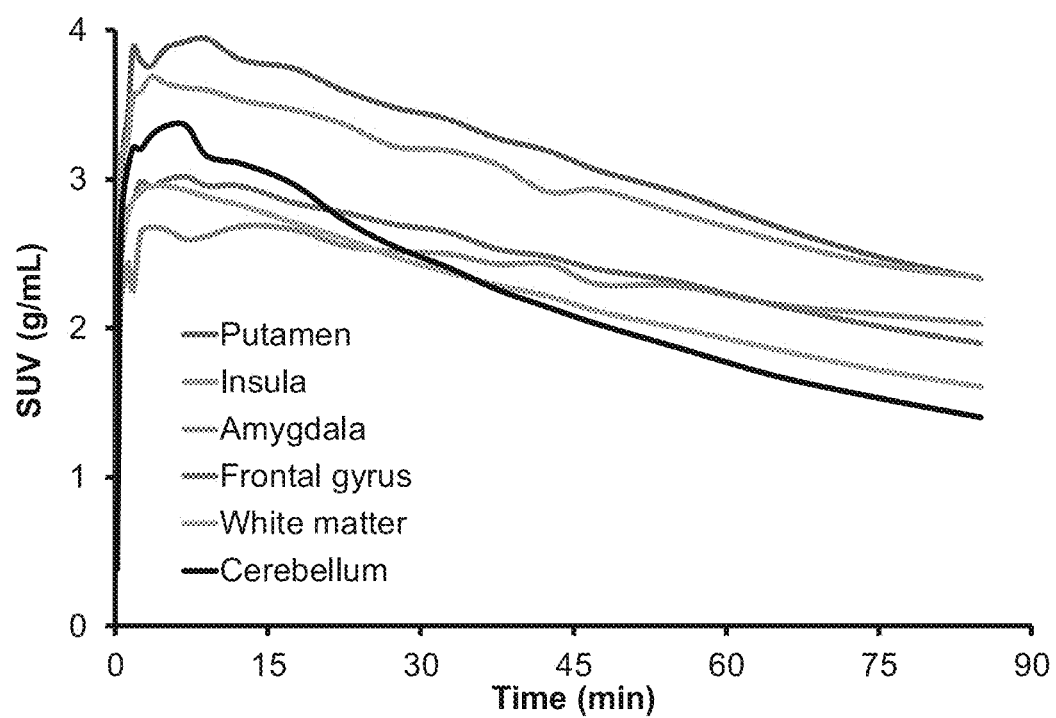
Figure 7:
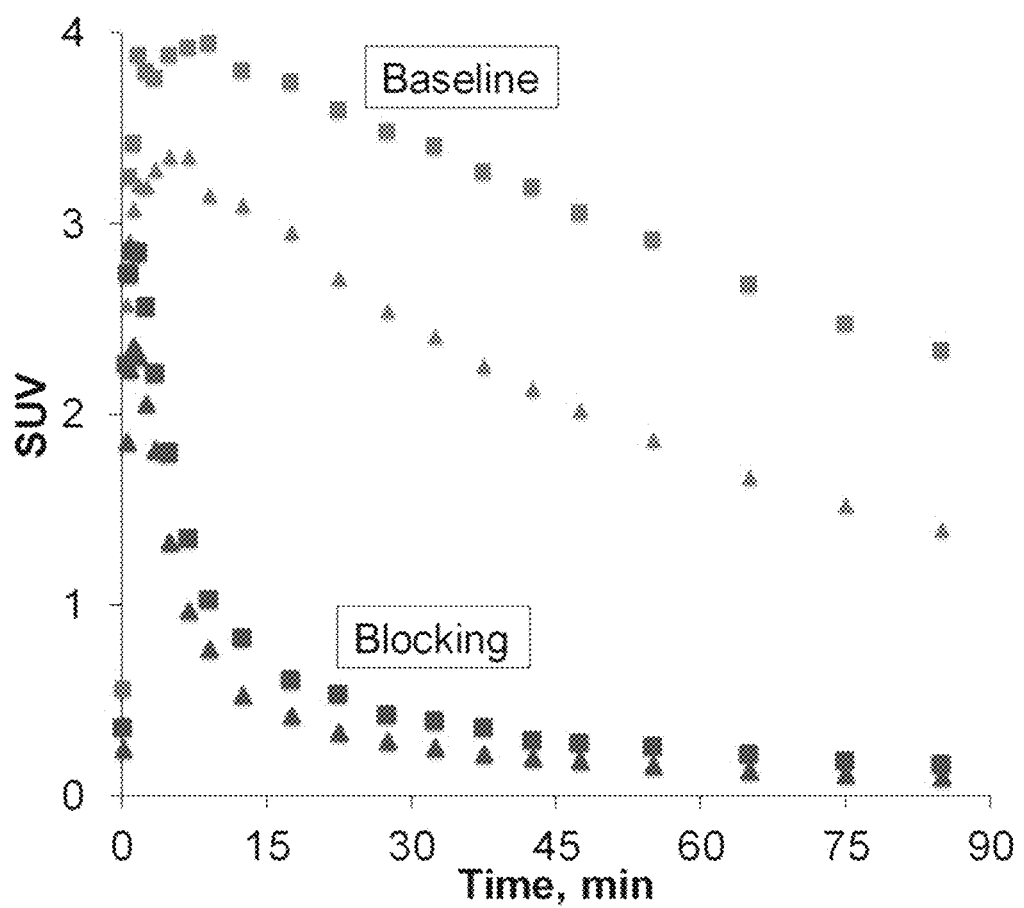
Figure 8:
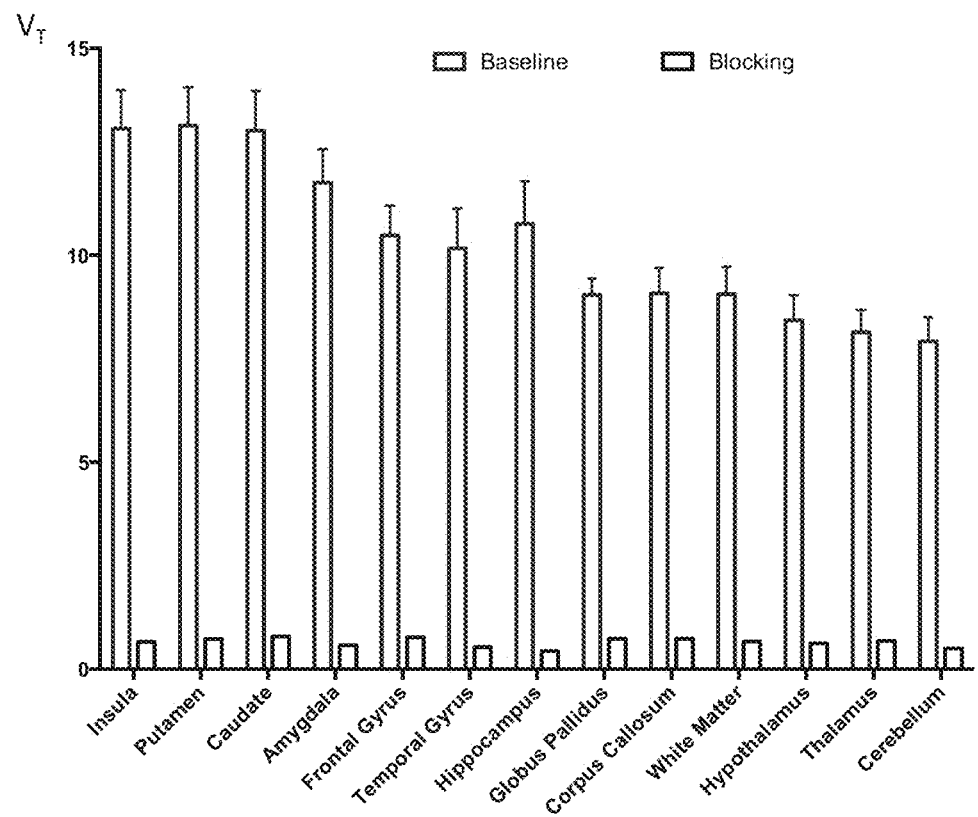
Figure 9:
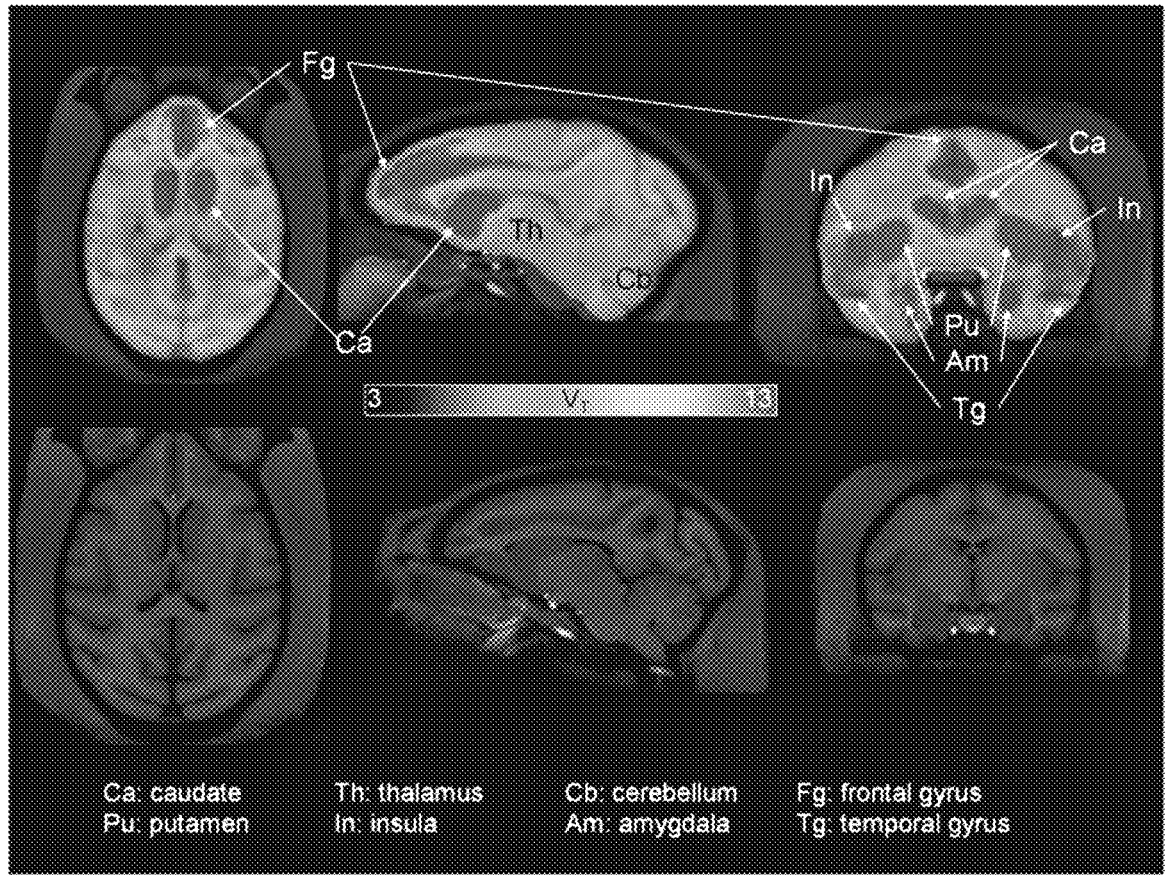
Figure 10:
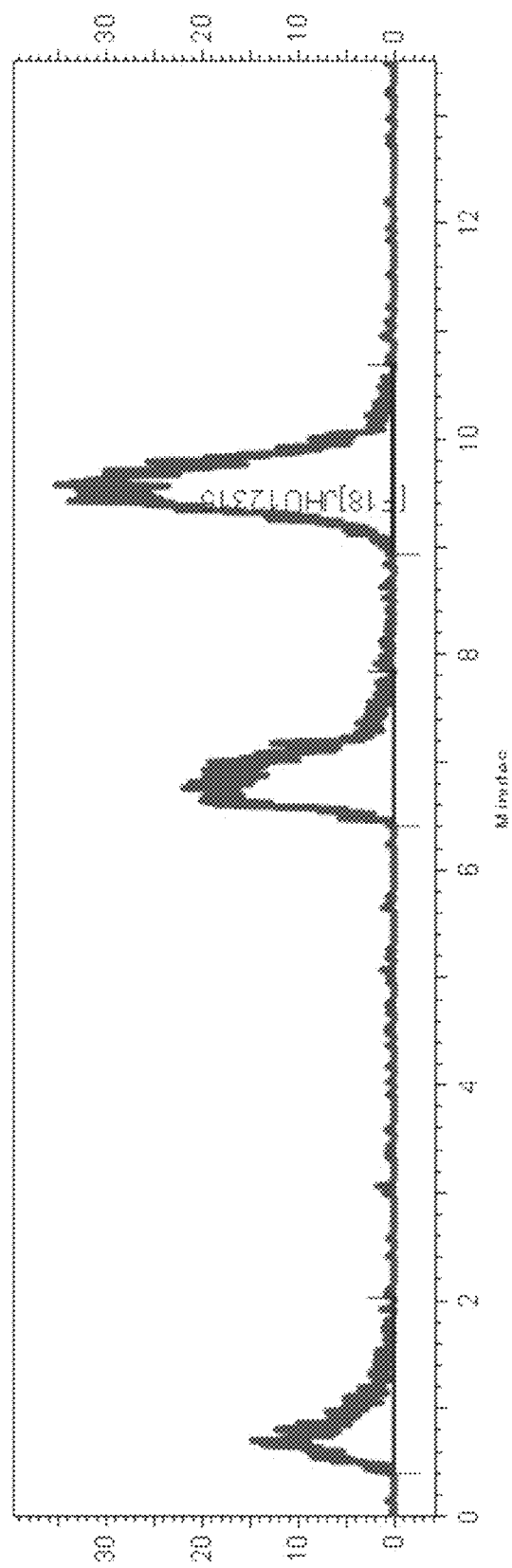
Figure 11:
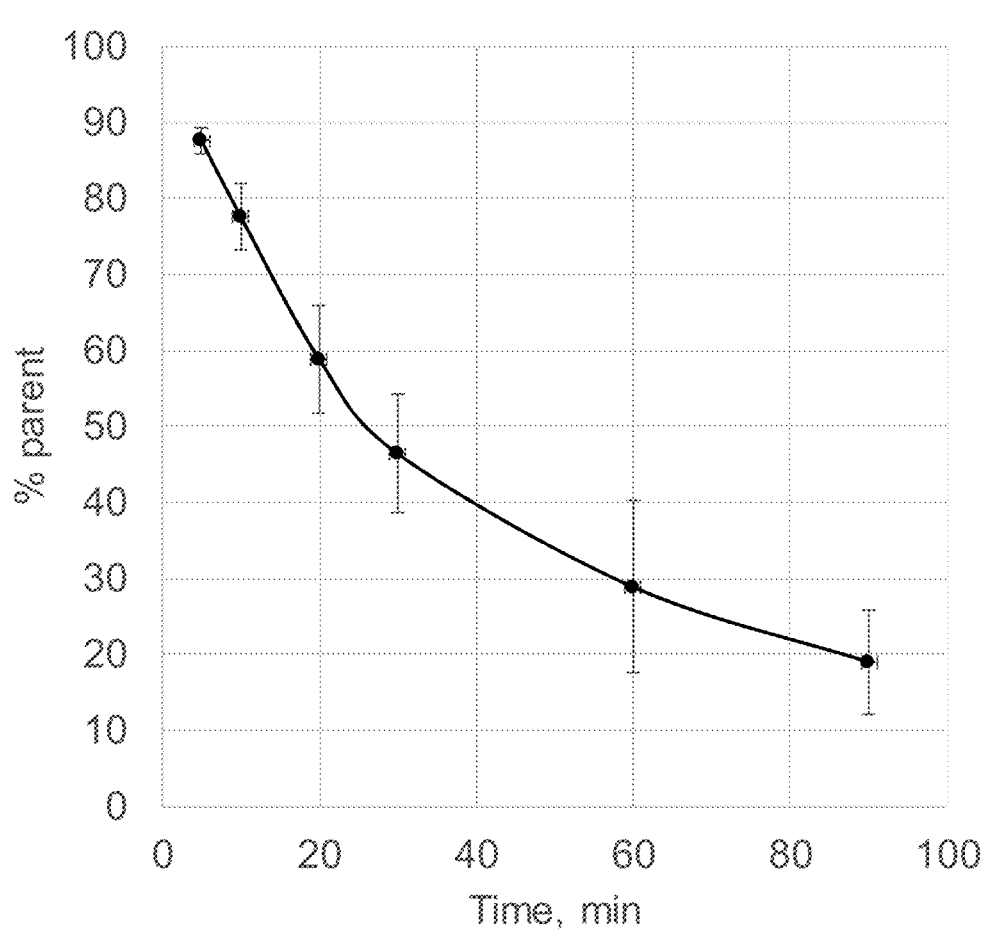

Having thus described the presently disclosed subject matter in general terms, reference will now be made to the accompanying Figures, which are not necessarily drawn to scale, and wherein:

FIG. 1A and FIG. 1B show (A) the synthesis of N-(3,3-diphenylpropyl)-6-fluoronicotinamide (FNDP) and precursor-FNDP for radiolabeling of [$^{18}$F]FNDP; reagents and conditions: (a) 1-[3-(dimethylamino)propyl]-3-ethylcarbodiimde, hydroxybenzotriazole (HOBt), N,N-diisopropylethylamine (DIPEA), dimethylformamide (DMF), room temperature; (B) the radiosynthesis of $^{18}$F-FNDP, a radiotracer for PET imaging of sEH;

FIG. 2 shows representative sEH inhibitors 1-cyclohexyl-3-dodecyl-urea (CDU) and 12-(3-(adamantan-1-yl)ureido) dodecanoic acid (AUDA) known in the art (Shen, *Expert. Opin. Ther. Pat.,* 2010); because of the large hydrophobic domains in their structures these compounds are considered unsuitable leads for PET radiotracer development;

FIG. 3 shows a comparative study of the relative fluorescence of compounds FNDP, nor-fluoro-FNDP (N-(3,3-diphenylpropyl)-nicotinamide) and AUDA; FNDP demonstrated low nanomolar inhibitory activity against sEH, comparable to that of AUDA and nor-fluoro-FNDP;

FIG. 4 shows the dose-dependent blocking of $^{18}$F-FNDP (0.1 mCi) uptake with the sEH inhibitor nor-fluoro-FNDP (subcutaneous) in the CD-1 mouse brain at 60 min after radiotracer injection; data are the mean % ID/g tissue±SD (n=3); abbreviations: Str, striatum; Ctx, cortex; Hip, hippocampus; CB, cerebellum; the blocking curve demonstrates that $^{18}$F-FNDP specifically labels sEH binding sites in all brain regions studied; the residual binding at the highest dose of the blocker corresponds to non-specific binding;

FIG. 5 shows the baseline and blocking of $^{18}$F-FNDP (0.1 mCi) uptake in sEH-KO and control C57BL/6 mice at 60 min post-injection of the radiotracer; data are the mean % ID/g±SD (n=5); blocking employed the sEH inhibitor nor-fluoro-FNDP (1 mg/kg, subcutaneous);

FIG. 6 shows the representative plasma time-activity curves (TACs) obtained from the baseline PET study in baboon; a total of 13 brain regions were analyzed, 6 of which were shown above for clarity;

FIG. 7 shows the comparison of regional time-uptake curves of $^{18}$F-FNDP at baseline (two upper curves) and after blockade (two lower curves) with nor-fluoro-FNDP (2 mg/kg) in the same baboon shows a striking reduction of radioactivity in the blocking scan; two representative regions, putamen (squares) and cerebellum (triangles), are shown;

FIG. 8 shows the comparisons of $^{18}$F-FNDP PET regional distribution volume ($V_T$) between baseline and blocking scans in the baboon brain for 13 brain regions; data=mean $V_T$±SD (baseline n=3, blocking n=1);

FIG. 9 shows the PET baseline (averaged, 3 scans, top row) and blocking (single scan, bottom row) parametric $V_T$ images of $^{18}$F-FNDP in baboon brain; the PET images, displayed with a pseudo color scale, were overlayed with the baboon's brain MR images (in gray scale);

FIG. 10 shows the representative radiometabolite HPLC of baboon plasma, 60 min time-point (parent $^{18}$F-FNDP—9.5 min, two radiometabolites—0.7 and 6.8 min); and FIG. 11 shows the HPLC radiometabolite analysis, time-% curve of parent $^{18}$F-FNDP in baboon plasma; data=mean % parent±SD, n=3.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. $^{18}$F-FNDP for Pet Imaging of Soluble Epoxide Hydrolase

Soluble epoxide hydrolase (sEH) is a bifunctional enzyme located within cytosol and peroxisomes that converts epoxides to the corresponding diols and hydrolyzes phosphate monoesters. It serves to inactivate epoxyeicosatrienoic acids (EETs), which have vasoactive and anti-inflammatory properties. Inhibitors of sEH are pursued as agents to mitigate neuronal damage after stroke. To date, however, many of the sEH inhibitors possess a large hydrophobic domain that makes them unlikely as viable radiotracers due to potentially high non-specific binging (FIG. 2). In the presently disclosed subject matter, the synthesis, the biodistribution and the baboon brain PET imaging of N-(3,3-diphenylpropyl)-6-$^{18}$F-fluoronicotinamide ($^{18}$F-FNDP) are presented. $^{18}$F-FNDP is a radiotracer for sEH that is structurally similar to the potent sEH inhibitor N-(3,3-diphenylpropyl)-nicotinamide, also known as nor-fluoro-FNDP (Eldrup et al., J. Med. Chem., 2009). $^{18}$F-FNDP readily enters mouse and baboon brain, and selectively labels sEH with dramatic specificity.

Presently, $^{18}$F-FNDP is the first and only radiotracer with suitable properties for PET imaging of sEH in animal brain.

A. Compounds of Formula (I)

Accordingly, in some embodiments, the presently disclosed subject matter provides a compound of formula (I):

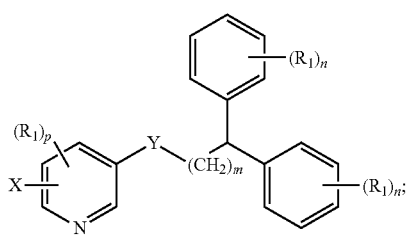

(I)

wherein X is selected from the group consisting of F, Br, and I, and radioisotopes thereof; Y is —NR—C(=O)— or —C(=O)—NR—; m is an integer selected from the group consisting of 1, 2, 3, and 4; n is an integer selected from the group consisting of 1, 2, 3, 4, and 5; p is an integer selected from the group consisting of 1, 2, and 3; R is selected from the group consisting of hydrogen, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; each $R_1$ can independently be the same or different and is selected from the group consisting of hydrogen, halogen, alkoxyl, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted alkylaryl, substituted or unsubstituted naphthyl, and substituted or unsubstituted biphenyl; and stereoisomers or pharmaceutically acceptable salts thereof.

In other embodiments, the compound of formula (I) is a compound of formula (II):

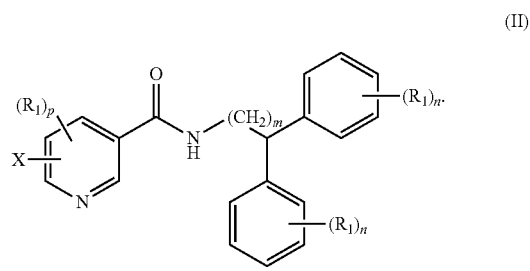

(II)

In particular embodiments, the compound of formula (I) comprises a radioactive isotope suitable for imaging. In more particular embodiments, the radioactive isotope suitable for imaging is selected from the group consisting of $^{18}$F, $^{76}$Br, $^{123}$I, $^{124}$I, $^{125}$I, and $^{131}$I. In yet more particular embodiments, the radioactive isotope suitable for imaging is $^{18}$F.

In still more particular embodiments, the compound of formula (I) is

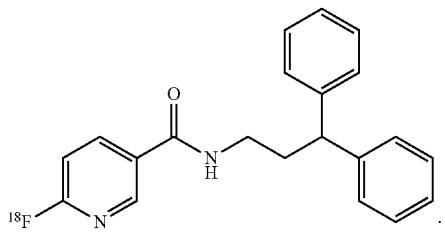

B. Methods of Using Compounds of Formula (I) for Imaging Soluble Epoxide Hydrolase (sEH)

In some embodiments, the presently disclosed subject matter provides a method for imaging soluble epoxide hydrolase (sEH), the method comprising contacting sEH with an effective amount of a compound of formula (I), and making an image, the compound of formula (I) comprising:

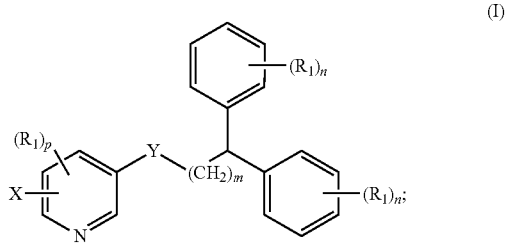

(I)

wherein:

X is selected from the group consisting of $^{18}$F, $^{76}$Br, $^{123}$I, $^{124}$I, $^{125}$I, and $^{131}$I; Y is —NR—C(=O)— or —C(=O)—NR—; m is an integer selected from the group consisting of 1, 2, 3, and 4; n is an integer selected from the group consisting of 1, 2, 3, 4, and 5; R is selected from the group consisting of hydrogen, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; $R_1$ is selected from the group consisting of hydrogen, halogen, alkoxyl, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted alkylaryl, substituted or unsubstituted naphthyl, and substituted or unsubstituted biphenyl; and stereoisomers or pharmaceutically acceptable salt thereof.

In some embodiments, the compound of formula (I) is a compound of formula (II):

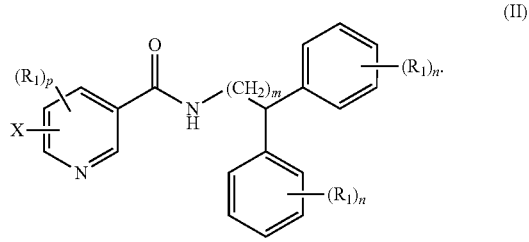

(II)

In particular embodiments, X is $^{18}F$.

In more particular embodiments, the compound of formula (I) is a compound of formula (II):

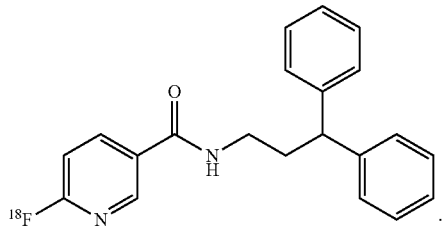 [SMILES: O=C(NCCC(c1ccccc1)c1ccccc1)c1ccc([18F])nc1]

Contacting" means any action which results in at least one compound comprising the imaging agent of the presently disclosed subject matter physically contacting sEH. Contacting can include exposing sEH to the compound in an amount sufficient to result in contact of at least one compound with sEH. The method can be practiced in vitro or ex vivo by introducing, and preferably mixing, the compound and sEH in a controlled environment, such as a culture dish or tube. The method can be practiced in vivo, in which case contacting means exposing sEH in a subject to at least one compound of the presently disclosed subject matter, such as administering the compound to a subject via any suitable route. According to the presently disclosed subject matter, contacting may comprise introducing, exposing, and the like, the compound at a site distant to sEH to be contacted, and allowing the bodily functions of the subject, or natural (e.g., diffusion) or man-induced (e.g., swirling) movements of fluids to result in contact of the compound and sEH.

By "making an image," it is meant using positron emission tomography (PET) to form an image of a cell, tissue, tumor, part of body, and the like.

In other embodiments, the compound of formula (I) is highly specific to sEH. In some embodiments, the specificity is up to about 95%.

In other embodiments, the sEH is in vitro, in vivo, or ex vivo. In yet other embodiments, sEH is present in a subject.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In some embodiments, a detectably effective amount of the imaging agent of the presently disclosed methods is administered to a subject. In accordance with the presently disclosed subject matter, "a detectably effective amount" of the imaging agent is defined as an amount sufficient to yield an acceptable image using equipment which is available for clinical use. A detectably effective amount of the imaging agent may be administered in more than one injection. The detectably effective amount of the imaging agent can vary according to factors such as the degree of susceptibility of the individual, the age, sex, and weight of the individual, idiosyncratic responses of the individual, the dosimetry, and instrument and film-related factors. Optimization of such factors is well within the level of skill in the art.

In particular embodiments, the compound of formula (I) is able to cross the blood-brain-barrier, that is, sEH is present in the brain of the subject. In other embodiments, the method is non-invasive.

The term "non-invasive" as used herein refers to methods where no instruments are introduced into the body.

It is preferable to have the compound comprising the imaging agent to localize to sEH quickly after administration so as to minimize any side effects to the subject. Accordingly, in some embodiments, the compound of formula (I) readily enters the brain of the subject.

In some embodiments, the presently disclosed methods use compounds that are stable in vivo such that substantially all, e.g., more than about 50%, 60%, 70%, 80%, or more preferably 90% of the injected compound is not metabolized by the body prior to excretion. In other embodiments, the compound comprising the imaging agent is stable in vivo.

It also is preferable that the compounds of the presently disclosed subject matter are excreted from tissues of the body quickly to prevent prolonged exposure to the radiation of the radiolabeled compound administered to the patient. Typically compounds of the presently disclosed subject matter are eliminated from the body in less than about 24 hours. More preferably, compounds of the presently disclosed subject matter are eliminated from the body in less than about 16 hours, 12 hours, 8 hours, 6 hours, 4 hours, or 2 hours.

C. Methods of Using Compounds of Formula (I) for Inhibiting Soluble Epoxide Hydrolase (sEH) in the Treatment of a sEH-Mediated Disease In other embodiments, the presently disclosed subject matter provides a method for inhibiting soluble epoxide hydrolase (sEH) in the treatment of a sEH mediated disease, the method comprising administering to a subject a therapeutically effective amount of a compound of formula (I), thereby inhibiting sEH.

As used herein, the term "inhibit" means to decrease or diminish the excess soluble epoxide hydrolase activity found in a subject. The term "inhibit" also may mean to decrease, suppress, attenuate, diminish, arrest, or stabilize the development or progression of a disease, disorder, or condition. Inhibition may occur, for e.g., by at least 10%, 20%, 30%, 40%, 50%, 60%, 70%, 80%, 90%, 95%, 98%, 99%, or even 100% compared to an untreated control subject or a subject without the disease or disorder.

As used herein, in general, the "effective amount" of an active agent refers to an amount sufficient to produce the desired effect, such as delivering the amount of active agent that can be detected in the brain or used for imaging, diagnosing, and/or treating the brain. A "therapeutically effective amount" of a therapeutic agent refers to the amount of the agent necessary to elicit the desired biological response. As will be appreciated by those of ordinary skill in the art, the effective amount of an agent may vary depending on such factors as the desired biological endpoint, the agent to be delivered, the composition of the pharmaceutical composition, the target tissue or cell, and the like. In some embodiments, the term "effective amount" refers to an amount sufficient to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

In particular embodiments, the soluble epoxide hydrolase mediated disease is selected from the group consisting of hypertension, atherosclerosis, inflammation, diabetes related diseases, pain, pulmonary diseases, Alzheimer's disease, vascular cognitive impairment (VCI), and stroke.

D. Pharmaceutical Compositions and Administration

In some embodiments, the present disclosure provides a pharmaceutical composition including one compound of formula (I), alone or in combination with one or more additional therapeutic agents in admixture with a pharmaceutically acceptable excipient. Accordingly, in some embodiments, the presently disclosed subject matter provides a pharmaceutical composition comprising a compound of formula (I), and a pharmaceutically acceptable carrier, diluent, or excipient. One of skill in the art will recognize that the pharmaceutical compositions include the pharmaceutically acceptable salts of the compounds described above.

Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids, such as arginate and the like, and salts of organic acids like glucuronic or galactunoric acids and the like (see, for example, Berge et al, "Pharmaceutical Salts," Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000).

In particular embodiments, the salt is a tri(hydrocarbyl) ammonium or tetra(hydrocarbyl)ammonium salt. In yet more particular embodiments, the salt is selected from the group consisting of a tri($C_1$-$C_8$-alkyl)ammonium, tetra($C_1$-$C_8$-alkyl)ammonium, triphenylammonium, tri(hydroxy-$C_1$-$C_8$-alkyl)ammonium, and tetra(hydroxy-$C_1$-$C_8$-alkyl)ammonium salt. In even more particular embodiments, the salt is selected from the group consisting of a trimethylammonium, triethylammonium, tri(hydroxyethyl)ammonium, tripropylammonium, and tri(hydroxypropyl)ammonium salt.

In therapeutic and/or diagnostic applications, the compounds of the disclosure can be formulated for a variety of modes of administration, including oral (sublingual, buccal), peroral, sublingual, systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid (e.g., solutions, suspensions, or emulsions) or solid dosage forms (capsules or tablets) and administered systemically or locally. The agents may be delivered, for example, in a timed-, controlled-, or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery. In some embodiments, the pharmaceutical composition is administered orally. In some embodiments, the pharmaceutical composition is administered intravenously. In some embodiments, the pharmaceutical composition is administered intramuscularly. In some embodiments, the pharmaceutical composition is administered intrathecally. In some embodiments, the pharmaceutical composition is administered subcutaneously.

For injection, the agents of the disclosure may be formulated and diluted in aqueous solutions, such as in physiologically compatible buffers, such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers, such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof, such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler, such as lactose, binders, such as starches, and/or lubricants such, as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

E. Kits

In yet other embodiments, the presently disclosed subject matter provides a kit comprising a compound of formula (I). In certain embodiments, the kit provides packaged pharmaceutical compositions comprising a pharmaceutically acceptable carrier, diluent, or excipient, and a presently disclosed compound. In certain embodiments the packaged pharmaceutical composition will comprise the reaction precursors necessary to generate the compound of the invention upon combination with a radio labeled precursor. Other packaged pharmaceutical compositions provided by the present invention further comprise indicia comprising at least one of: instructions for preparing compounds according to the invention from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

The descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C$_1$-C$_{10}$ means one to ten carbons, including 1, 2, 3, 4, 5, 6, 7, 8, 9, and 10 carbons). In particular embodiments, the term "alkyl" refers to C$_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, acylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)— $CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$); —CH=CH—CH=CH—; —CH=CH—$CH_2$—; —$CH_2CH_2CH_2CH_2$—, —$CH_2CH$=$CHCH_2$—, —$CH_2C$≡$CCH_2$—, —$CH_2CH_2CH$($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

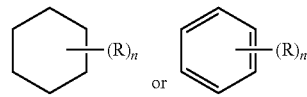

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

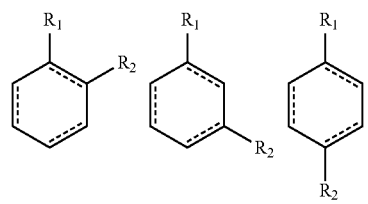

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol (  ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', —NR'R—SR', -halogen, —SiR'R"R'", —OC(O)R', —C(O)R', —CO$_2$R', —C(O) NR'R", —OC(O)NR'R", —NR"C(O)R', —NR'—C(O) NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR)$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R" wherein R' and R" are each independently selected from the group consisting of alkyl groups. The term trialkylamino refers to a group having the structure —NR'R"R''', wherein R', R", and R''' are each independently selected from the group consisting of alkyl groups. Additionally, R', R", and/or R''' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Overview

Soluble epoxide hydrolase (sEH) is a bifunctional enzyme located within cytosol and peroxisomes that converts epoxides to the corresponding diols and hydrolyzes phosphate monoesters. It serves to inactivate epoxyeicosatrienoic acids (EETs), which have vasoactive and anti-inflammatory properties. Inhibitors of sEH are pursued as agents to mitigate neuronal damage after stroke. The presently disclosed subject matter provides N-(3,3-diphenylpropyl)-6-$^{18}$F-fluoronicotinamide ($^{18}$F-FNDP) and analogs and derivatives thereof, which proved highly specific for imaging of sEH in the mouse and non-human primate brain with PET.

$^{18}$F-FNDP was synthesized from the corresponding bromo-precursor. sEH inhibitory activity of $^{18}$F-FNDP was measured using the sEH Inhibitor Screening Assay Kit (Cayman Chemical, MI). Biodistribution was undertaken in CD-1 mice. Binding specificity was assayed in CD-1 and sEH knock-out mice and *Papio anubis* (baboon) through pre-treatment with an sEH inhibitor to block sEH binding. Dynamic PET imaging with arterial blood sampling was performed in three baboons with regional tracer binding quantified using distribution volume ($V_T$). Metabolism of $^{18}$F-FNDP in baboon was assessed using high performance liquid chromatography (HPLC).

$^{18}$F-FNDP ($K_i$=1.73 nM) was prepared in one step in radiochemical yield of 14±7%, specific radioactivity in the range of 888-3,774 GBq/μmol and in radiochemical purity >99% using an automatic radiosynthesis module. The time of preparation was about 75 min. In CD-1 mice, regional uptake followed the pattern of striatum>cortex>hippocampus>cerebellum, consistent with the known brain distribution of sEH, with 5.2 percent injected dose per gram of tissue at peak uptake. Blockade of 80-90% was demonstrated in all brain regions. Minimal radiotracer uptake was present in sEH-KO mice. PET baboon brain distribution paralleled that seen in mouse with marked blockade (95%) noted in all regions indicating sEH-mediated uptake of $^{18}$F-FNDP. Two hydrophilic metabolites were identified with 20% parent compound present at 90 min post-injection in baboon plasma.

$^{18}$F-FNDP can be synthesized in suitable radiochemical yield and high specific radioactivity and purity. In vivo imaging experiments demonstrated that $^{18}$F-FNDP targeted sEH in murine and non-human primate brain specifically. $^{18}$F-FNDP is a promising PET radiotracer likely to be useful for understanding the role of sEH in a variety of conditions affecting the central nervous system.

Example 2

Material and Methods

All reagents were used directly as obtained commercially from Sigma-Aldrich (St. Louis, Mo.). Nor-fluoro-FNDP was prepared as described previously (Edrup et al. J. Med. Chem. 2009). Column flash chromatography was carried out using E. Merck silica gel 60F (230-400 mesh) (Sigma-Aldrich). $^1$H NMR spectra were recorded on a Bruker-500 MHz NMR spectrometer (Billerica, Mass.), in CDCl$_3$ (referenced to internal Me$_4$Si at $\delta_H$ 0 ppm). The high performance liquid chromatography (HPLC) system consisted of two Varian ProStar pumps (Palo Alto, Calif.), a single Rheodyne Model 7725i manual injector, a ProStar 325 UV-Vis variable wavelength detector, and a BioScan Flow-Count radioactivity detector (Poway, Calif.). Analytical and semi-preparative chromatography was performed using Phenomenex Luna C-18 10 μm columns (4.6×250 mm and 10×250 mm, respectively) (Torrance, Calif.). The experimental animal protocols were approved by the Animal Care and Use Committee of the Johns Hopkins Medical Institutions.

Synthesis.

N-(3,3-diphenylpropyl)-6-fluoronicotinamide (FNDP)

3,3-Diphenylpropan-1-amine (105.5 mg, 0.5 mmol) was added to a solution of 6-fluoronicotinic acid (70.5 mg, 0.5 mmol) in 3 mL N,N-dimethylformamide and followed by the addition of 1-hydroxybenzotriazole (135 mg, 1 mmol), 1-[3-(dimethylamino)propyl]-3-ethylcarbodiimde hydrochloride (191 mg, 1 mmol), and diisopropylethylamine (195.5 mg, 1.5 mmol). The reaction was stirred at room temperature for 48 h, the solvent was evaporated under vacuum and the residue was separated by flash LC (silica gel, hexane-ethylacetate 5:1→2:1) to give the desired product, FNDP (121 mg, 72%). $^1$H NMR (CHCl$_3$-d$_3$, 500 MHz) δ 8.32 (d, J=2.5 Hz, 1H), 8.10-8.06 (m, 1H), 7.27-7.24 (m, 8H), 7.25 (m, 2H), 7.01-6.98 (m, 1H), 5.92 (broad s, 1H), 4.07 (t, J=8 Hz, 1H), 3.57 (m, 2H), 2.48 (m, 2H).

6-Bromo-N-(3,3-diphenylpropyl)nicotinamide (Precursor-FNDP)

Precursor-FNDP was prepared similarly to FNDP using 6-bromonicotinic acid as the starting material. Yield: 59%. $^1$H NMR (CHCl$_3$-d$_3$, 500 MHz) δ 8.45 (d, J=2.5 Hz, 1H), 7.79 (m, 1H), 7.56 (d, J=8 Hz, 1H), 7.37-7.32 (m, 8H), 7.27-7.24 (m, 2H), 5.92 (broad s, 1H), 4.07 (t, J=9 Hz, 1H), 3.56 (m, 2H), 2.49 (m, 2H).

Radiosynthesis.

N-(3,3-diphenylpropyl)-6-$^{18}$F-fluoronicotinamide ($^{18}$F-FNDP)

A solution of $^{18}$F-fluoride obtained from proton bombardment of $^{18}$O-water in a General Electric PETtrace cyclotron and 2 mg of K$_2$CO$_3$ in 0.4 mL of water and 15-20 mg of Kryptofix 222® in 2 mL acetonitrile were added to a reaction vessel of a GE MicroLab module (Cincinnati, Ohio). The mixture was evaporated azeotropically at 140° C. under a stream of argon after the addition of 2 mL of CH$_3$CN. A solution of the precursor-FNDP (2 mg) in DMSO (0.8 mL) was added to the reaction vessel with the mixture heated at 160° C. for 12 min. The reaction mixture was cooled, diluted with 0.7 mL of water, and injected onto the reverse-phase semi-preparative high performance liquid chromatography (HPLC) column. The radioactive product peak was collected in 50 mL of HPLC grade water. The water solution was transferred through an activated Waters C-18 Sep-Pak light cartridge (Milford, Mass.). After washing the cartridge with 10 mL saline, the product was eluted with 1 mL of ethanol through a 0.2 μM sterile filter into a sterile, pyrogen-free vial and 10 mL of 0.9% saline was added through the same filter. The final product $^{18}$F-FNDP was then analyzed by analytical HPLC to determine the radiochemical purity and specific radioactivity. The total preparation time including quality control was 75 min. Semi-preparative HPLC conditions: Luna C18, 10 micron, 10×250 mm; mobile phase: 45:55 (acetonitrile: 0.1 M aqueous ammonium formate); flow rate 10 mL/min; UV—254 nm; retention time 13 min and 21 min (FNDP and precursor-FNDP, respectively). Analytical HPLC conditions: Luna C18, 10 micron, 4.6×250 mm; mobile phase: 55:45 (acetonitrile: 0.1 M aqueous ammonium formate); flow rate 3 mL/min; UV—254 nm; retention time 3.9 min and 6.5 min (FNDP and precursor-FNDP, respectively).

In Vitro Studies.

In vitro inhibition of sEH with FNDP. Inhibitory activity of FNDP and nor-fluoro-FNDP, an analogue of FNDP and known inhibitor of sEH (Eldrup et al., *J. Med. Chem.,* 2009), was measured using the sEH Inhibitor Assay Kit (Cayman Chemical, MI). In brief, $IC_{50}$ values of the sEH inhibitors were determined by measuring the inhibition of hydrolysis of (3-phenyl-oxiranyl)-acetic acid cyano-(6-methoxy-naphthalen-2-yl)-methyl ester by sEH. AUDA (Cayman Chemical, MI), a known inhibitor of sEH (Imig et al., *Hypertension,* 2005), was used as a positive control. All reactions were done in triplicate and the data were analyzed using GraphPad Prism (GraphPad Software, San Diego, Calif.) and inhibitory constants ($K_i$ values) were generated.

Biodistribution Studies with $^{18}$F-FNDP in Mice.

Baseline study in CD1 mice. Male, CD-1 mice weighing 25-27 g from Charles River (Wilmington, Mass.) were used. The animals were sacrificed by cervical dislocation at 5, 15, 30, 60 and 90 min following injection of 3.7 MBq (0.1 mCi) $^{18}$F-FNDP (specific radioactivity=814 GBq/μmol (22,000 mCi/μmol) in 0.2 mL saline into a lateral tail vein (n=3). The brains were removed and dissected on ice. Striatum, cortex, hippocampus, hypothalamus, cerebellum and the rest of brain were weighed and their radioactivity content was determined in a γ-counter LKB/Wallac 1283 CompuGamma CS (Perkin Elmer, Bridgeport, Conn.). Aliquots of the injectate were prepared as standards and their radioactivity content was determined along with the tissue samples. The percent of injected dose per gram of tissue (% ID/g tissue) was calculated.

Blocking of $^{18}$F-FNDP Binding in CD1 Mice.

In vivo binding specificity (blocking) studies were carried out by subcutaneous administration of various doses (0 mg/kg, 0.03 mg/kg, 0.3 mg/kg, 1 mg/kg, 3 mg/kg) of nor-fluoro-FNDP followed by IV injection of 3.7 MBq (0.1 mCi) $^{18}$F-FNDP 15 min thereafter (n=3). Ninety minutes after administration of the radiotracer the animals were sacrificed by cervical dislocation, brain tissues were harvested, and their radioactivity content was determined.

Baseline and Blocking Studies of $^{18}$F-FNDP in sEH Knock-Out (SEH-KO) and C57BL/6 Control Mice.

The baseline and blockade studies (nor-fluoro-FNDP, 1 mg/kg, subcutaneous) with the same batch of $^{18}$F-FNDP were performed similarly to the studies described above. sEH-KO mice (Ephx2 gene deletion; Jackson Labs) and C57B1/6 background strain mice were studied (n=5). All animals were sacrificed at 60 min after radiotracer injection.

The sample size of CD-1 and sEH-KO mice in the baseline and blocking studies was 3 and 5, respectively that corresponds to the statistical power value >0.9 as calculated by G*Power, v.3.1.9.2 freeware.

Baboon PET and Radiometabolite Studies

Dynamic baseline and blocking PET experiments (90 min) were performed on three male baboons (*Papio anubis*) weighing 23.9, 25.0 and 28.2 kg, using the High Resolution Research Tomograph (HRRT, CPS Innovations, Inc., Knoxville, Tenn.). In brief, the dynamic PET acquisition was performed in with an intravenous injection of 248 MBq (6.7 mCi) $^{18}$F-FNDP (specific radioactivity value of 2634 GBq/μmol (71,177 mCi/μmol), carrier mass=0.0011 μg/kg). For the blocking scan in the same baboon, nor-fluoro-FNDP (2 mg/kg) was given subcutaneously 1 h prior to the intravenous bolus injection of 307 MBq (8.3 mCi) $^{18}$F-FNDP (specific radioactivity value of 1420 GBq/μmol (38,386 mCi/μmol), carrier mass=0.0025 μg/kg) and the start of the scan. Radiometabolite analysis in baboon arterial blood was performed under the general conditions published previously (Hilton et al., *Nucl. Med. Biol.,* 2000).

Baboon PET Studies.

PET experiments were performed on a male baboon (*Papio anubis*) weighing 28.2 kg, using the High Resolution Research Tomograph (HRRT, CPS Innovations, Inc., Knoxville, Tenn.). The animal underwent one baseline PET scan and one blocking scan 3 weeks later. The animal was fasted for 12 h prior to each PET study. Anesthesia was induced with intramuscular ketamine (7.5-10 mg/kg) and maintained with a continuous intravenous infusion of propofol at 0.3-0.4 mg/kg/min throughout the PET experiment. One venous catheter was inserted for the radioligand injection, and one arterial catheter inserted to obtain arterial blood samples. Measurement of the arterial plasma input function was conducted through collection of 43 blood samples over the course of the 90 min dynamic PET scan. The baboon was also intubated to facilitate respiration, and circulatory volume was maintained by constant infusion of isotonic saline. Physiological vital signs including heart rate, blood pressure, electrocardiogram, and oxygen saturation were monitored continuously throughout the study.

The animal was positioned in the PET scanner with the head immobilized with a thermoplastic mask. A 6 min transmission scan was acquired using a rotating [$^{137}$Cs] cesium source for attenuation correction. The 90-min dynamic PET acquisition was then started in three-dimensional list mode simultaneously with an intravenous bolus injection of 248 MBq (6.7 mCi) $^{18}$F-FNDP (specific radioactivity value of 2634 GBq/μmol (71,177 mCi/μmol)). For the blocking scan, nor-fluoro-FNDP (2 mg/kg) was given subcutaneously 1 h prior to the intravenous bolus injection of 307 MBq (8.3 mCi) $^{18}$F-FNDP (specific radioactivity value of 1420 GBq/μmol (38,386 mCi/μmol) and the start of the 90-min dynamic PET imaging.

PET Image Reconstruction.

The 90 min PET list mode data were binned into 22 frames (three 20 s, two 30 s, two 1 min, three 2 min, eight 5 min, and four 10 min frames). The data were then reconstructed using the iterative ordered subsets expectation maximization (OS-EM) algorithm (with six iterations and 16 subsets), with correction for radioactive decay, dead time, attenuation, scatter and randoms. The attenuation maps were generated from 6 min transmission scans performed with a [$^{137}$Cs] cesium point source prior to the emission scans. The reconstructed image space consisted of cubic voxels, each 1.22 mm$^3$ in size, and spanning dimensions of 31 cm×31 cm (transaxially) and 25 cm (axially).

Brain Volumes of Interest (VOIs) and Regional Time-Activity Curves (TACs):

The software package PMOD (v3.3, PMOD Technologies Ltd, Zurich, Switzerland) was used for the following image processing and subsequent kinetic analysis steps. The previously acquired brain MRI T1-weighted images for the baboon were co-registered to the reconstructed dynamic PET images acquired in this study. Through manually matching the co-registered MRI to the INIA19 Template and NeuroMaps Atlas for Primate Brain Image Parcellation and Spatial Normalization (Rohlfing et al., Frontiers in neuroinformatics, 2012), 13 representative baboon brain VOIs were defined, including frontal and temporal gyms, thalamus, hippocampus, caudate, putamen, amygdala, globus pallidus, insula, hypothalamus, cerebellum, corpus callosum, and white matter. Brain regional TACs were then generated for both baseline and blocking PET scans using those VOIs.

PET Kinetic Analysis: Calculation of Brain Regional Distribution Volume ($V_T$):

Based on the regional TACs obtained above, $^{18}$F-FNDP binding to sEH was quantitatively characterized with the use of the metabolite-corrected arterial plasma input function. Following the consensus nomenclature for in vivo imaging of reversibly binding radioligands (Innis et al., *J. Cereb. Blood Flow Metab.*, 2007), due to the lack of a non-displaceable reference region, the main outcome measure was regional distribution volume ($V_T$), defined as the ratio of the concentration of the radioligand in regional brain tissue to that in plasma at equilibrium. Regional $V_T$ is proportional to the receptor density in the defined VOL $V_T$ was calculated using the Logan graphical method for each VOI (Logan et al., *J. Cereb. Blood Flow Metab.*, 1990).

Radiometabolite HPLC Analysis:

Baboon arterial blood samples were collected at very short intervals (<5 s) initially and gradually at prolonged intervals throughout the PET study for determination of plasma radioactivity. Selected samples taken at 0, 5, 10, 20, 30, 60, and 90 min were analyzed by HPLC for the presence of $^{18}$F-FNDP and its radioactive metabolites (FIG. 9) using the general method described previously (Hilton et al., *Nucl. Med. Biol.*, 2000). Briefly, 3 mL of plasma in 8 M urea was passed through a capture column (19×4.6 mm Strata-X, Phenomenex, Torrance, Calif.), followed by 1% acetonitrile in water to wash plasma proteins from the column. The effluent from the capture column, containing only highly polar components, flowed through a dual BGO detector (Bioscan, Washington, D.C.). The solvent was then switched to a mixture of 60% acetonitrile/40% 0.1 M aqueous ammonium formate pH=2.7 (2 mL/min) to elute the radiolabeled components bound to the capture column onto the analytical column (Gemini C18, 4.6×254 mm, Phenomenex, Torrance, Calif.).

Example 3

Chemistry

N-(3,3-diphenylpropyl)-6-fluoronicotinamide (FNDP) and N-(3,3-diphenylpropyl)-6-bromonicotinamide (precursor-FNDP) were synthesized with high yield (59-72%) (FIG. 1A). The molecular structures of FNDP and precursor-FNDP were confirmed by NMR analysis.

$^{18}$F-FNDP was prepared by nucleophilic radiofluorination of the bromo precursor-FNDP in a radiochemical yield of 14±7% (n=6) (non-decay-corrected), specific radioactivity in the range of 888-3,774 GBq/mmol (24,000-102,000 mCi/μmol) at the time synthesis ended and in a radiochemical purity greater than 99% (FIG. 1B). The final product, $^{18}$F-FNDP, was formulated as a sterile, apyrogenic solution in 7% ethanolic saline with a pH of 5.5-6.5.

FNDP exhibited $IC_{50}$ and $K_i$ values comparable to the potent sEH inhibitor AUDA. $IC_{50}$ values of FNDP, nor-fluoro-FNDP and AUDA were 8.66±0.06, 18.53±0.04 and 6.48±0.05 nM, respectively (FIG. 3). The corresponding $K_i$ values of FNDP, nor-fluoro-FNDP and AUDA were 1.73, 3.71, and 1.30 nM, respectively.

Example 4

Regional Brain Distribution Studies in CD-1 Mice

Baseline Study.

The regional distribution of $^{18}$F-FNDP in the CD-1 mouse brain is shown in Table 1.

TABLE 1

Regional distribution of 18F-FNDP in CD-1 mouse brain
(mean % ID/g tissue ± SD, n = 3)

| Region | 5 min | 15 min | 30 min | 60 min | 90 min |
|---|---|---|---|---|---|
| Striatum | 5.24 ± 0.45 | 3.29 ± 0.36 | 2.32 ± 0.15 | 1.07 ± 0.14 | 0.54 ± 0.07 |
| Cortex | 4.69 ± 0.21 | 2.92 ± 0.36 | 2.07 ± 0.05 | 0.87 ± 0.14 | 0.45 ± 0.05 |
| Hippocampus | 3.29 ± 0.54 | 2.51 ± 0.34 | 1.76 ± 0.15 | 0.81 ± 0.15 | 0.43 ± 0.06 |
| Rest of brain | 3.53 ± 0.11 | 2.37 ± 0.34 | 1.64 ± 0.06 | 0.71 ± 0.10 | 0.38 ± 0.04 |
| Hypothalamus | 2.59 ± 0.18 | 1.66 ± 0.28 | 1.04 ± 0.08 | 0.51 ± 0.07 | 0.31 ± 0.05 |
| Cerebellum | 2.75 ± 0.11 | 1.31 ± 1.01 | 1.09 ± 0.16 | 0.52 ± 0.07 | 0.29 ± 0.04 |

SEH Binding Specificity of $^{18}$F-FNDP-Dose-Escalation Blocking in CD-1 Mice.

The sEH inhibitor nor-fluoro-FNDP blocked the $^{18}$F-FNDP binding in all studied brain regions (striatum, hippocampus, cortex and cerebellum) at 60 min post-injection in a dose-dependent fashion (FIG. 4). At the highest blocker dose of 3 mg/kg the reduction of radioactivity uptake in the striatum, hippocampus and cortex was about 90% and in the cerebellum about 75%.

Baseline and Blocking Studies of $^{18}$F-FNDP IN SEH KO and C57BL6 Control Mice.

In the baseline experiment at 60 min post-injection the regional uptake of $^{18}$F-FNDP in the C57BL6 control mice was about 1 percent of the injected dose per gram of tissue (% ID/g) in the striatum, hippocampus and cortex and 0.5% ID/g in the cerebellum (FIG. 5). In the blocking experiment in the C57BL6 mice the $^{18}$F-FNDP brain uptake was reduced to ~0.2% ID/g tissue in all regions studied. In sEH-KO mice the regional brain uptake of $^{18}$F-FNDP at 60 min was nearly the same in the baseline (0.11-0.12% ID/g) and blocking experiments (0.10-0.11% ID/g) (FIG. 5).

Example 5

PET Imaging in *Papio anubis*

High and heterogeneous uptake of radioactivity into the baboon brain was observed during the baseline scan after bolus injection of $^{18}$F-FNDP, evident by the representative regional TACs (FIG. 6). All regional TACs peaked at about 5 min post-injection, with peak SUVs ranging from 2.5 to 4.0 g/mL. The peak SUV of the entire brain was 3.2 and gradually reduced to 1.8 at the end of the 90 min dynamic scan. The highest accumulation of radioactivity occurred in regions such as putamen, insula, frontal cortex and amygdala, and lower uptake was seen in the white matter and cerebellum. Notably, the time-activity curves of the cerebellum decreased more rapidly than other regions studied (FIG. 6).

When quantified using $V_T$, among the 13 brain volumes of interest investigated, the highest radioligand binding occurred in the insula, putamen, caudate, and amygdala ($V_T$>10.0), with intermediate uptake in frontal/temporal gyrus, hippocampus, and globus pallidus ($V_T$>8.3), followed by corpus callosum, white matter, hypothalamus, and thalamus ($V_T$>7.2). The lowest binding was in the cerebellum, with a $V_T$ of 6.97.

The TAC comparisons between baseline and blocking studies are shown in FIG. 7. During the blocking study, the regional TACs peaked much earlier, at about 1 min post-injection, with an average peak SUV of 2.3 g/mL over the entire brain, and decreased rapidly to an average SUV of only 0.18 g/mL (10%) of the baseline value—at the end of the 90 min scan. When quantified by $V_T$ all regions in the blockade scan showed $V_T$<0.8, and reductions of more than 90% when compared to the baseline $V_T$ values. The percentage reductions were comparable between high and low binding regions identified during the baseline study, e.g., insula and amygdala at 95% reduction, while cerebellum demonstrated 93% reduction (FIG. 8). Parametric $V_T$ images were generated for both baseline and blocking scans for comparisons (FIG. 9).

The specific radioactivity of $^{18}$F-FNDP doses in the blockade and baseline baboon studies ranged between 1420 GBq/μmol and 2634 GBq/μmol. Because the specific activity was so high the corresponding FNDP carrier mass was only 0.0011-0.0025 μg/kg that is 6-orders of magnitude lower than the nor-fluoro-FNDP blocker dose (2 mg/kg). Without wishing to be bound to any one particular theory, it was therefore assumed that the specific radioactivity variability does not affect the results of this study.

Radiometabolite analysis of blood samples from baboon using reverse-phase high-performance liquid chromatography (RP-HPLC) showed that the parent compound $^{18}$F-FNDP was metabolized to two hydrophilic species (FIG. 10). The combined radiometabolites in the plasma reached values of 80% in baboon at 90 min post-injection (FIG. 10 and FIG. 11).

Example 6

Summary and Discussion

Due to the lack of available radiotracers only about 39 of the hundreds of known binding sites (receptors and enzymes) in the human brain have been imaged by PET (CNS radiotracer table). Until now sEH was one of the numerous binding sites lacking a specific PET radiotracer. With the substantial number of sEH inhibitors developed by the pharmaceutical industry and researchers from academia, the opportunities for sEH PET radiotracer development are wide open. However, many potent sEH inhibitors possess a large hydrophobic domain that make them unlikely as viable radiotracers due to potentially high non-specific binding (FIG. 2).

In the presently disclosed subject matter, N-(3,3-diphenylpropyl)-6-fluoronicotinamide was synthetized (FNDP, FIG. 1A), a potent sEH inhibitor with molecular properties (log P of 2.9 and molecular weight MW of 334 Da) that are optimal for brain PET radiotracers (Horti et al., Springer, 2014). FNDP is structurally similar to the sEH inhibitor N-(3,3-diphenylpropyl)-nicotinamide (nor-fluoro-FNDP) that was identified by Boehringer Ingelheim as an sEH inhibitor (human $IC_{50}$ of 7 nM) with improved "drug-like" characteristics (Eldrup et al., J. Med. Chem., 2009) and was used here as a lead compound for development of FNDP and blocker in animal experiments. In vitro assay demonstrated that FNDP is a sEH inhibitor with greater potency than that of the lead nor-fluoro-FNDP and comparable to the common sEH inhibitor AUDA (FIG. 3).

FNDP contains a fluorine-atom in position 2 of the pyridine ring that is activated for nucleophilic substitution and can be readily radiofluorinated via a corresponding bromo-precursor under the general conditions of a Br-pyridine for $^{18}$F-pyridine exchange that were developed previously (Gao et al., J. Med. Chem., 2008). Radiosynthesis of N-(3,3-diphenylpropyl)-6-$^{18}$F-fluoronicotinamide ($^{18}$F-FNDP) was performed in a conventional FDG-radiochemistry module by the nucleophilic radiofluorination of precursor-FNDP (FIG. 1B) followed by the semi-preparative HPLC separation and formulation of the final radiolabeled product as sterile apyrogenic solutions in saline. The radiotracer was prepared with very high specific radioactivity and radiochemical purity. The precursor-FNDP was readily separated by preparative HPLC and was not detectable in the final product $^{18}$F-FNDP by analytical HPLC.

Mouse Studies.

In CD-1 mice $^{18}$F-FNDP exhibited a heterogeneous pattern of brain uptake, comparable to the expected regional expression of sEH in the mouse brain (Marowsky et al., Neuroscience, 2009). The peak uptake value was 5.2% ID/g at 5 min post-injection, followed by a rapid decline. That brain uptake is considered to be moderately high as uptake of 1% ID/g has traditionally been used as the minimum criterion for selection of investigational central nervous system radiotracers at our PET Center. Among the brain regions studied the highest accumulation of $^{18}$F-FNDP radioactivity occurred in the striatum, cortex, hippocampus and rest of brain, while lower but considerable radioactivity was seen in the hypothalamus and cerebellum (Table 1). The mouse brain distribution is comparable with in vitro data (Marowsky et al., Neuroscience, 2009).

Two types of studies were performed for demonstration of the specificity of $^{18}$F-FNDP binding, namely, dose-escalation blockade in CD-1 mice and biodistribution in sEH knock-out (sEH-KO) mice. The regional brain uptake of $^{18}$F-FNDP in CD-1 mice, a common strain for testing PET tracers, was highly sensitive to escalating doses of the sEH inhibitor nor-fluoro-FNDP (FIG. 4). The blocked binding in CD-1 mouse brain is considered to be specific (90% in the striatum, hippocampus and cortex), whereas the residual binding at the high dose of the blocker is considered to be non-specific binding (10%). These findings indicate that $^{18}$F-FNDP uptake in the mouse brain is highly specific and mediated by sEH. The study did not reveal a region with low sEH binding. The 75% blocking of radioactivity in the cerebellum is consistent with expression of sEH in this region (Marowsky et al., Neuroscience, 2009) and suggests that cerebellum may not be able to be used as a reference in the mouse brain.

As a further test of binding specificity, sEH-KO mice and control animals with the same genetic background (C57BL/

6) (Sinal et al., *J. Biol. Chem.*, 2000) were employed. Because the sEH-KO mouse brain is devoid of sEH Qin et al., *Mol. Neurobiol.*, 2015) it was expected that $^{18}$F-FNDP binding in these mice would be non-specific and that the difference between sEH-KO and control brain uptake would represent specific sEH binding. Uptake of $^{18}$F-FNDP was compared in the baseline experiments in sEH-KO and control animals (C57BL/6) at 60 min after radiotracer injection (FIG. 5). There was a marked reduction of $^{18}$F-FNDP uptake (about 90%) in the sEH-KO mice as compared with controls. High values of control/sEH-KO ratio were demonstrated in all regions tested (10.3—striatum, 9.4—cortex, 9.2—hippocampus, 4.8—cerebellum). Furthermore, the reduction of $^{18}$F-FNDP uptake in sEH-KO mice was negligible in a blockade study employing the sEH inhibitor nor-fluoro-FNDP (FIG. 4). That negligble effect indicated that any non-specific binding of $^{18}$F-FNDP to other proteins, such as the product of the Ephx1 gene (microsomal epoxide hydrolase) (Marowsky et al., *Neuroscience*, 2009), was negligible in the sEH-KO brain. In the C57BL/6 controls the blocking effect (about 80%) (FIG. 5) proved quite similar to that in CD-1 mice (FIG. 4).

The mouse studies demonstrated that $^{18}$F-FNDP readily entered the brain (5% ID/g at peak) and labeled cerebral sEH in two strains of control mice (CD-1 and C57BL/6) with a high degree of specificity (80-90%). In agreement to the low expression of sEH in the KO animals, the brain uptake of $^{18}$F-FNDP in the sEH-KO mice was 10-fold lower than that in the controls and is essentially non-specific.

Baboon PET Imaging.

High and rapid heterogeneous uptake of radioactivity into the baboon brain was observed during three baseline $^{18}$F-FNDP PET scans in three different animals (FIG. 9). The regional distribution of $^{18}$F-FNDP in the baboon brain agrees with semi-quantitative assessment of sEH expression in the human (Sura et al., *J. Histochem. Cytochem*, 2008), and mouse brain (Marowsky et al., *Neuroscience*, 2009). The regional TACs confirmed characteristics of optimally reversible PET radioligand binding. Notably, the washout rate of $^{18}$F-FNDP in the baboon brain (FIG. 6) was less rapid than that in the mouse brain (Table 1) and robust for mathematical modeling (see below).

The blocking PET studies demonstrated that $^{18}$F-FNDP labeled sEH in baboon brain with very high specificity (FIG. 7, FIG. 8, and FIG. 9). Blocking was observed in all baboon brain regions investigated, including cerebellum.

Soluble epoxide hydrolase inhibitors can increase peripheral vasodilation and reduce blood pressure, which may, in turn, increase the cerebral blood flow and affect radiotracer delivery. To examine that possibility, radiotracer kinetics were modeled using the classic two-tissue-three-compartment model from which the rate constant for transfer from arterial plasma to tissue ($K_1$) can be reliably estimated. It was found that the average $K_1$ values at baseline and blocking were 0.18 and 0.14 ml/cm$^3$/min, respectively, a 23% difference. That observation demonstrated that the $K_1$ changes cannot be attributed as the source for the marked reductions (>90%) of $V_T$ values from baseline to blocking, confirming that $^{18}$F-FNDP labeled sEH in the baboon brain with very high specificity. The presently disclosed subject matter did not reveal a reference region in the baboon brain that was non-displaceable and free of sEH binding, in agreement with broad abundance of sEH in the mammalian brain (Sura et al., *J. Histochem. Cytochem*, 2008; Marowsky et al., *Neuroscience*, 2009).

The analysis of radiometabolites in baboon plasma demonstrated that $^{18}$F-FNDP was metabolized to two hydrophilic radiometabolites. By the end of the 90 min PET scan the remaining parent $^{18}$F-FNDP represented ~20% of the radioactivity in plasma, comparable to many other PET radiotracers. Because the radiometabolites were hydrophilic, they are unlikely to enter the brain to an appreciable extent, suggesting that kinetic modeling of radiometabolites may be unnecessary for quantification of sEH.

$^{18}$F-FNDP, the first specific PET radiotracer for imaging of sEH has been developed. $^{18}$F-FNDP, a potent sEH inhibitor, readily entered the mouse (5% ID/g tissue) and baboon (SUV=4) brain and radiolabeled sEH with very high specificity (up to 95%) in both animal species while exhibiting reversible brain kinetics amenable to quantitative analysis. $^{18}$F-FNDP holds promise for further pre-clinical studies and human PET imaging to evaluate the role of sEH in a variety of conditions and disorders including VCI, mild cognitive impairment and stroke.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Couto P J, Millis R M. PET Imaging of Epigenetic Influences on Alzheimer's Disease. *International journal of Alzheimer's disease*. 2015; 2015:575078;

CNS Radiotracer Table (http://www.nimh.nih.gov/research-priorities/therapeutics/cns-radiotracer-table.shtml) 2015;

Eldrup A B, Soleymanzadeh F, Taylor S J, et al. Structure-based optimization of arylamides as inhibitors of soluble epoxide hydrolase. *J Med Chem*. 2009; 52:5880-5895;

Gao Y, Kuwabara H, Spivak C E, et al. Discovery of (−)-7-Methyl-2-exo-[3'-(6-[18F] fluoropyridin-2-yl)-5'-pyridinyl]-7-azabicyclo[2.2.1]heptane, a Radiolabeled Antagonist for Cerebral Nicotinic Acetylcholine Receptor (α4β2-nAChR) with Optimal Positron Emission Tomography Imaging Properties. *J Med Chem*. 2008; 51:4751-4764;

Heiss W D. PET imaging in ischemic cerebrovascular disease: current status and future directions. *Neurosci Bull*. 2014; 30:713-732;

Hilton J, Yokoi F, Dannals R F, Ravert H T, Szabo Z, Wong D F. Column-switching HPLC for the analysis of plasma in PET imaging studies. *Nucl Med Biol*. 2000; 27:627-630;

Horti A G, Raymont V, Terry G E. PET imaging of endocannabinoid system. In: Dierckx R, Otte A, De Vries E F, Van Waarde A, eds. *PET and SPECT of Neurobiological Systems*. Berlin-Heidelberg: Springer; 2014:251-319;

Hung Y W, Hung S W, Wu Y C, et al. Soluble epoxide hydrolase activity regulates inflammatory responses and seizure generation in two mouse models of temporal lobe epilepsy. *Brain Behav Immun.* 2015; 43:118-129;

Iliff J J, Wang R, Zeldin D C, Alkayed N J. Epoxyeicosanoids as mediators of neurogenic vasodilation in cerebral vessels. *American journal of physiology Heart and circulatory physiology.* 2009; 296:H1352-1363;

Iliff J J, Alkayed N J. Soluble Epoxide Hydrolase Inhibition: Targeting Multiple Mechanisms of Ischemic Brain Injury with a Single Agent. *Future neurology.* 2009; 4:179-199;

Imig J D, Zhao X, Zaharis C Z, et al. An orally active epoxide hydrolase inhibitor lowers blood pressure and provides renal protection in salt-sensitive hypertension. *Hypertension.* 2005; 46:975-981;

Inceoglu B, Zolkowska D, Yoo H J, et al. Epoxy fatty acids and inhibition of the soluble epoxide hydrolase selectively modulate GABA mediated neurotransmission to delay onset of seizures. *PLoS One.* 2013; 8:e80922;

Ingraham R H, Gless R D, Lo H Y. Soluble epoxide hydrolase inhibitors and their potential for treatment of multiple pathologic conditions. *Curr Med Chem.* 2011; 18:587-603;

Innis R B, Cunningham V J, Delforge J, et al. Consensus nomenclature for in vivo imaging of reversibly binding radioligands. *J Cereb Blood Flow Metab.* 2007; 27:1533-1539;

Knopman D S, Parisi J E, Boeve B F, et al. Vascular dementia in a population-based autopsy study. *Arch Neurol.* 2003; 60:569-575;

Lee C R, North K E, Bray M S, et al. Genetic variation in soluble epoxide hydrolase (EPHX2) and risk of coronary heart disease: The Atherosclerosis Risk in Communities (ARIC) study. *Hum Mol Genet.* 2006; 15:1640-1649;

Logan J, Fowler J S, Volkow N D, et al. Graphical analysis of reversible radioligand binding from time-activity measurements applied to [N-11C-methyl]-(−)-cocaine PET studies in human subjects. *J Cereb Blood Flow Metab.* 1990; 10:740-747;

Marowsky A, Burgener J, Falck J R, Fritschy J M, Arand M. Distribution of soluble and microsomal epoxide hydrolase in the mouse brain and its contribution to cerebral epoxyeicosatrienoic acid metabolism. *Neuroscience.* 2009; 163:646-661;

Martini R P, Ward J, Siler D A, et al. Genetic variation in soluble epoxide hydrolase: association with outcome after aneurysmal subarachnoid hemorrhage. *J Neurosurg.* 2014; 121:1359-1366;

Morris E, Chalkidou A, Hammers A, Peacock J, Summers J, Keevil S. Diagnostic accuracy of F amyloid PET tracers for the diagnosis of Alzheimer's disease: a systematic review and meta-analysis. *Eur J Nucl Med Mol Imaging.* 2015;

Morris E, Chalkidou A, Hammers A, Peacock J, Summers J, Keevil S. Diagnostic accuracy of F amyloid PET tracers for the diagnosis of Alzheimer's disease: a systematic review and meta-analysis. *Eur J Nucl Med Mol Imaging.* 2015; 43:374-385;

Newman J W, Morisseau C, Hammock B D. Epoxide hydrolases: their roles and interactions with lipid metabolism. *Prog Lipid Res.* 2005; 44:1-51;

Nelson J W, Young J M, Borkar R N, et al. Role of soluble epoxide hydrolase in age-related vascular cognitive decline. *Prostaglandins Other Lipid Mediat* 2014; 113-115:30-37;

Qin X, Wu Q, Lin L, et al. Soluble Epoxide Hydrolase Deficiency or Inhibition Attenuates MPTP-Induced Parkinsonism. *Mol Neurobiol.* 2015; 52:187-195;

Rohlfing T, Kroenke C D, Sullivan E V, et al. The INIA19 Template and NeuroMaps Atlas for Primate Brain Image Parcellation and Spatial Normalization. *Frontiers in neuroinformatics.* 2012; 6:27;

Shen H C, Hammock B D. Discovery of inhibitors of soluble epoxide hydrolase: a target with multiple potential therapeutic indications. *J Med Chem.* 2012; 55:1789-1808;

Shen H C. Soluble epoxide hydrolase inhibitors: a patent review. *Expert Opin Ther Pat.* 2010; 20:941-956;

Silbert L C, Dodge H H, Perkins L G, et al. Trajectory of white matter hyperintensity burden preceding mild cognitive impairment. *Neurology.* 2012; 79:741-747;

Sinal C J, Miyata M, Tohkin M, Nagata K, Bend J R, Gonzalez F J. Targeted disruption of soluble epoxide hydrolase reveals a role in blood pressure regulation. *J Biol Chem.* 2000; 275:40504-40510;

Spector A A, Norris A W. Action of epoxyeicosatrienoic acids on cellular function. *Am J Physiol Cell Physiol.* 2007; 292:C996-1012;

Sura P, Sura R, Enayetallah A E, Grant D F. Distribution and expression of soluble epoxide hydrolase in human brain. *J Histochem Cytochem.* 2008; 56:551-559;

Terashvili M, Tseng L F, Wu H E, et al. Antinociception produced by 14,15-epoxyeicosatrienoic acid is mediated by the activation of beta-endorphin and met-enkephalin in the rat ventrolateral periaqueductal gray. *J Pharmacol Exp Ther.* 2008; 326:614-622;

White L, Petrovitch H, Hardman J, et al. Cerebrovascular pathology and dementia in autopsied Honolulu-Asia Aging Study participants. *Ann N Y Acad Sci.* 2002; 977:9-23.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I)

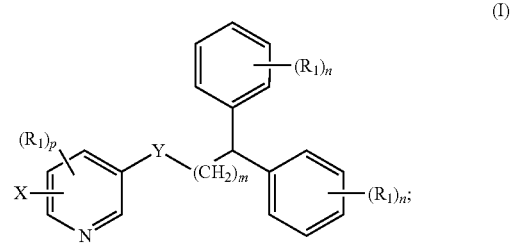

wherein

X is a radioactive isotope selected from the group consisting of $^{18}$F, $^{76}$Br, $^{123}$I, $^{124}$I, $^{125}$I, and $^{131}$I;

Y is —NR—C(=O)— or —C(=O)—NR—;

m is an integer selected from the group consisting of 1, 2, 3, and 4;

n is an integer selected from the group consisting of 1, 2, 3, 4, and 5;

p is an integer selected from the group consisting of 1, 2, and 3;

R is selected from the group consisting of hydrogen, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;

each $R_1$ can independently be the same or different and is selected from the group consisting of hydrogen, halogen, alkoxyl, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted alkylaryl, substituted or unsubstituted naphthyl, and substituted or unsubstituted biphenyl;

and stereoisomers or pharmaceutically acceptable salts thereof.

2. The compound of claim 1, wherein the compound of formula (I) is a compound of formula (II):

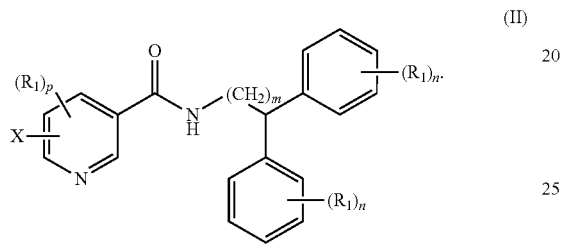

3. The compound of claim 1, wherein the radioactive isotope $^{18}$F.

4. The compound of claim 1, wherein the compound of formula (I) is

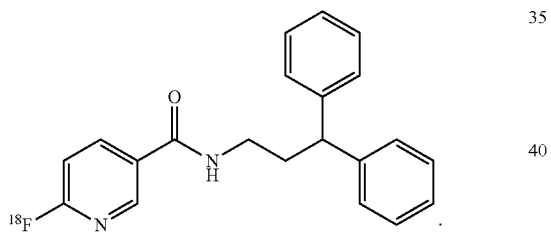

5. A method for imaging soluble epoxide hydrolase (sEH), the method comprising administering and/or contacting sEH with an effective amount of a compound of formula (I), and making an image, the compound of formula (I) comprising:

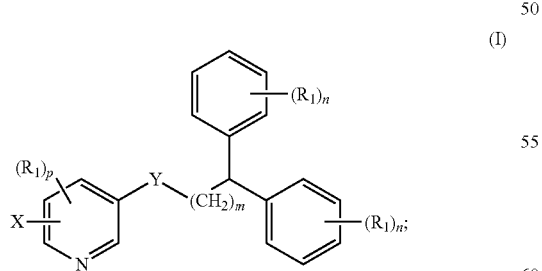

wherein:
X is selected from the group consisting of $^{18}$F, $^{76}$Br, $^{123}$I, $^{124}$I, $^{125}$I, and $^{131}$I;
Y is —NR—C(=O)— or —C(=O)—NR—;
m is an integer selected from the group consisting of 1, 2, 3, and 4;

n is an integer selected from the group consisting of 1, 2, 3, 4, and 5;
p is an integer selected from the group consisting of 1, 2, and 3;
R is selected from the group consisting of hydrogen, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;
each $R_1$ can independently be the same or different and is selected from the group consisting of hydrogen, halogen, alkoxyl, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted alkylaryl, substituted or unsubstituted naphthyl, and substituted or unsubstituted biphenyl;
and stereoisomers or pharmaceutically acceptable salts thereof.

6. The method of claim 5, wherein the compound of formula (I) is a compound of formula (II):

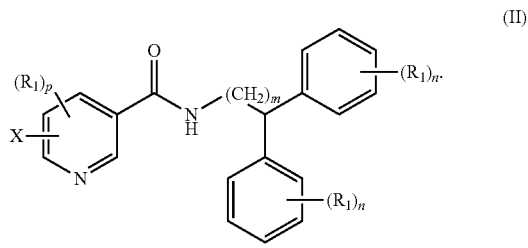

7. The method of claim 5, wherein X is $^{18}$F.

8. The method of claim 5, wherein the compound of formula (I) is:

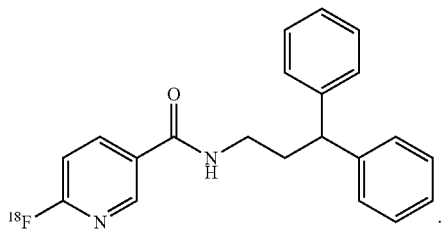

9. The method of claim 5, wherein the image is obtained by using positron emission tomography.

10. The method of claim 5, wherein the compound of formula (I) is highly specific to sEH.

11. The method of claim 10, wherein the specificity is up to about 95%.

12. The method of claim 5, wherein sEH is in vitro, in vivo, or ex vivo.

13. The method of claim 5, wherein sEH is present in a subject.

14. The method of claim 13, when the subject is human.

15. The method of claim 13, wherein the compound of formula (I) is able to cross the blood-brain-barrier and wherein sEH is present in the brain of the subject.

16. The method of claim 13, wherein the method is non-invasive.

17. The method of claim 13, wherein the compound of formula (I) readily enters the brain of the subject.

18. The method of claim 13, wherein the compound of formula (I) is cleared from the brain of the subject.

19. A method for inhibiting soluble epoxide hydrolase (sEH) in the treatment of a sEH-mediated disease, the method comprising administering to a subject a therapeutically effective amount of a compound of formula (I), thereby inhibiting sEH.

20. The method of claim 19, wherein the soluble epoxide hydrolase mediated disease is selected from the group consisting of hypertension, atherosclerosis, inflammation, diabetes related diseases, pain, pulmonary diseases, Alzheimer's disease, vascular cognitive impairment (VCI), and stroke.

21. A pharmaceutical composition comprising a compound according to claim 1, and a pharmaceutically acceptable carrier, diluent, or excipient.

22. A kit comprising a packaged pharmaceutical composition comprising a compound according to claim 1.

* * * * *